United States Patent [19]

Tominaga et al.

[11] 4,414,390
[45] Nov. 8, 1983

[54] CARBOSTYRIL COMPOUNDS AND COMPOSITIONS CONTAINING SAME

[75] Inventors: Michiaki Tominaga; Yang Yung-hsiung; Hidenori Ogawa; Kazuyuki Nakagawa, all of Tokushima, Japan

[73] Assignee: Otsuka, Pharmaceutical Co., Ltd., Tokyo, Japan

[21] Appl. No.: 403,582

[22] PCT Filed: Nov. 11, 1981

[86] PCT No.: PCT/JP81/00328

§ 371 Date: Jul. 12, 1982

§ 102(e) Date: Jul. 12, 1982

[87] PCT Pub. No.: WO82/01706

PCT Pub. Date: May 27, 1982

[30] Foreign Application Priority Data

Nov. 11, 1980 [JP] Japan .................................. 55/159016
Dec. 18, 1980 [JP] Japan .................................. 55/179950

[51] Int. Cl.³ ............................................ C07D 471/04
[52] U.S. Cl. ..................................... 546/121; 424/258
[58] Field of Search ........................................ 546/121

[56] References Cited

FOREIGN PATENT DOCUMENTS 55-53284  4/1980  Japan .

Primary Examiner—Jane T. Fan
Attorney, Agent, or Firm—Sughrue, Mion, Zinn, Macpeak and Seas

[57] ABSTRACT

A carbostyril compound of the formula (I)

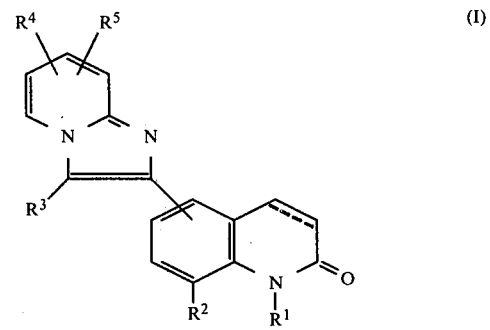

wherein the values of the substituents are as defined in the description, and pharmaceutically acceptable salts thereof, composition containing the compound of the formula (I) or its pharmaceutically acceptable salt as an active ingredient, and process for preparing same. The compound of the formula (I) and its pharmaceutically acceptable salts have cardiotonic effects.

17 Claims, No Drawings

CARBOSTYRIL COMPOUNDS AND COMPOSITIONS CONTAINING SAME

BACKGROUND ART

This invention relates to certain carbostyril compounds and to pharmaceutically acceptable salts thereof which are useful as cardiotonic agents, processes for preparing the same, and pharmaceutical compositions containing the carbostyril compounds or salts thereof.

Various carbostyril compounds are known which have hypotensive, blood platelet coagulation inhibitory or antiallergic activity as described in Japanese Patent Application (OPI) Nos. 130589/79, 135785/79, 138585/79, 141785/79, 76872/80, 49319/80, 53283/80, 53284/80 and 83781/80 (the term "OPI" as used herein refers to a "published unexamined Japanese patent application").

Further, EP-A1-7525 and EP-A1-8014 describe isoquinoline compounds which have cardiac and circulatory activities.

However, the carbostyril compounds of this invention are structurally different from the conventional carbostyril and isoquinoline compounds.

DISCLOSURE OF THE INVENTION

One object of this invention is to provide carbostyril compounds having a cardiotonic activity.

Another object of this invention is to provide a pharmaceutical composition containing the carbostyril compound in a cardiotonically effective amount.

A further object of this invention is to provide a process for preparing a carbostyril compound and its pharmaceutically acceptable salts thereof.

As a result of extensive research, this invention has been accomplished which, in one aspect, provides a carbostyril compound of the formula (I)

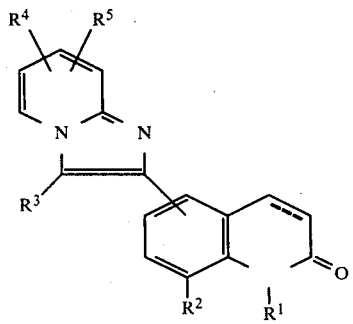

wherein $R^1$ represents a hydrogen atom, a lower alkyl group, a lower alkenyl group, a lower alkynyl group, or a phenyl-lower alkyl group;

$R^2$ represents a hydrogen atom, a lower alkyl group, a lower alkoxy group, a halogen atom, or a hydroxy group;

$R^3$ represents a hydrogen atom, a lower alkyl group, a halogen atom, a nitroso group, an amino group which may be substituted with a lower alkyl group, a lower alkanoylamino group, an N,N-di-lower alkylaminomethyl group, a carbamoylmethyl group, a cyanomethyl group, or a carboxymethyl group;

$R^4$ and $R^5$, which may be the same or different, each represents a hydrogen atom, a halogen atom, a lower alkyl group, a hydroxy group, a lower alkoxy group, or a nitro group;

the bonding between the 3- and 4-positions of the carbostyril nucleus is a single bond or a double bond; and the position at which the imidazopyridyl group of the formula

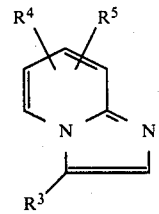

is attached to the carbostyril nucleus is the 5- or 6-position;

with the proviso that when the imidazopyridyl group is attached to the 5-position of the carbostyril nucleus, $R^2$ should not be a hydrogen atom, a lower alkyl group, or a halogen atom; or its pharmaceutically acceptable salt.

In another aspect, this invention provides a cardiotonic composition containing a compound of the formula (I) or a pharmaceutically acceptable salt thereof in a cardiotonically effective amount.

In a further aspect, this invention provides processes for preparing the compounds of the formula (I) and pharmaceutically acceptable salts thereof.

BEST MODE FOR CARRYING OUT THE INVENTION

The compounds of the formula (I) above and pharmaceutically acceptable salts thereof have heart muscle contraction stimulating effect or positive inotropic effect and coronary blood flow increasing activity, and are useful as a cardiotonic agent for treating heart diseases such as congestive heart failure and the like. They are advantageous in that they do not or only slightly, if any, increase heart beats.

The term "lower alkyl" as used herein refers to a straight or branched chain alkyl group having 1 to 6 carbon atoms such as a methyl group, an ethyl group, a propyl group, an isopropyl group, a butyl group, a tert-butyl group, a pentyl group, a hexyl group and the like.

The term "phenyl-lower alkyl" as used herein refers to a phenyl-lower alkyl group having a straight or branched chain alkyl group having 1 to 6 carbon atoms in the alkyl moiety such as a benzyl group, a 2-phenylethyl group, a 1-phenylethyl group, a 3-phenylpropyl group, a 4-phenylbutyl group, a 1,1-dimethyl-2-phenylethyl group, a 5-phenylpentyl group, a 6-phenylhexyl group, a 2-methyl-3-phenylpropyl group and the like.

The term "lower alkenyl" as used herein refers to a straight or branched chain alkenyl group having 2 to 6 carbon atoms such as a vinyl group, an allyl group, a crotyl group, a 1-methylallyl group, a 3-butenyl group, a 2-pentenyl group, a 3-pentenyl group, a 4-pentenyl group, a 2-methyl-3-butenyl group, a 1-methyl-3-butenyl group, a 2-hexenyl group, a 3-hexenyl group, a 4-hexenyl group, a 5-hexenyl group, a 2-methyl-4-pentenyl group, a 1-methyl-4-pentenyl group, a 2-methyl-3-pentenyl group, a 1-methyl-3-pentenyl group and the like.

The term "lower alkynyl" as used herein refers to a straight or branched chain alkynyl group having 2 to 6 carbon atoms such as an ethynyl group, a 2-propynyl group, a 1-propynyl group, a 2-butynyl group, a 3-butynyl group, a 2-pentynyl group, a 3-pentynyl group, a 4-pentynyl group, a 2-methyl-3-butynyl group, a 1-methyl-3-butynyl group, a 2-hexynyl group, a 3-hexynyl group, a 4-hexynyl group, a 5-hexynyl group, a 2-methyl-4-pentynyl group, a 1-methyl-4-pentynyl group, a 2-methyl-3-pentynyl group, a 1-methyl-3-pentynyl group and the like.

The term "halogen" as used herein refers to a halogen atom such as chlorine, bromine, iodine and fluorine.

The term "amino group which may be substituted with a lower alkyl group" as used herein refers to an amino group and an amino group substituted with 1 or 2 of a straight or branched chain lower alkyl group having 1 to 6 carbon atoms such as a methylamino group, an ethylamino group, a propylamino group, an isopropylamino group, a butylamino group, a tert-butylamino group, a pentylamino group, a hexylamino group, an N,N-dimethylamino group, an N,N-diethylamino group, an N-methyl-N-ethylamino group, an N-methyl-N-propylamino group, an N-ethyl-N-isopropylamino group, an N,N-dipropylamino group, an N-methyl-N-butylamino group, an N-ethyl-N-tert-butylamino group, an N,N-dibutylamino group, an N-methyl-N-pentylamino group, an N-propyl-N-pentylamino group, an N,N-dipentylamino group, an N-methyl-N-hexylamino group, an N-butyl-N-hexylamino group, an N,N-dihexylamino group and the like.

The term "N,N-di-lower alkylaminomethyl" as used herein refers to an N,N-di-lower alkylaminomethyl group having a straight or branched chain alkyl group having 1 to 6 carbon atoms in each alkyl moiety thereof such as an N,N-dimethylaminomethyl group, an N-methyl-N-ethylaminomethyl group, an N,N-diethylaminomethyl group, an N-methyl-N-propylaminomethyl group, an N-ethyl-N-isopropylaminomethyl group, an N,N-dipropylaminomethyl group, an N-methyl-N-butylaminomethyl group, an N-ethyl-N-tert-butylaminomethyl group, an N,N-dibutylaminomethyl group, an N-methyl-N-pentylaminomethyl group, an N-propyl-N-pentylaminomethyl group, an N,N-dipentylaminomethyl group, an N-methyl-N-hexylaminomethyl group, an N-butyl-N-hexylaminomethyl group, an N,N-dihexylaminomethyl group and the like.

The term "lower alkanoylamino" as used herein refers to a straight or branched chain lower alkanoylamino group having 1 to 6 carbon atoms such as a formamido group, an acetamido group, a propionylamino group, a butyrylamino group, an isobutyrylamino group, a valerylamino group, an isovalerylamino group, a hexanoylamino group and the like.

The term "lower alkoxy" as used herein refers to a straight or branched chain alkoxy group having 1 to 6 carbon atoms such as a methoxy group, an ethoxy group, a propoxy group, an isopropoxy group, a butoxy group, a tert-butoxy group, a pentyloxy group, a hexyloxy group and the like.

The compounds of this invention of the formula (I) can be prepared by various alternative procedures. A preferred example thereof is a process according to Reaction Scheme-1 below.

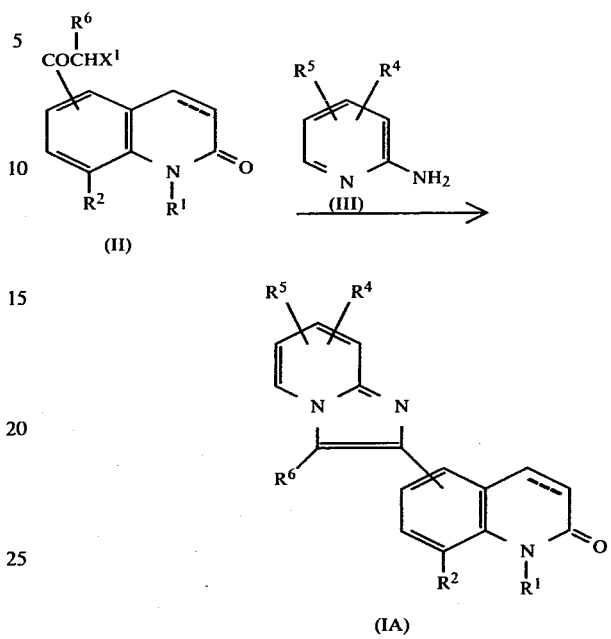

Reaction Scheme-1

In the above formulae, $X^1$ represents a halogen atom and $R^6$ represents a hydrogen atom or a lower alkyl group and $R^1$, $R^2$, $R^4$, $R^5$ and the bonding between the 3- and 4-positions of the carbostyril nucleus have the same meanings as defined above.

In the formula (II), examples of the halogen atom represented by $X^1$ include chlorine, fluorine, bromine and iodine.

The reaction between the compound of the formula (II) and the compound of the formula (III) which is a known compound can be carried out in the absence of solvents or in the presence of an appropriate solvent, preferably in the presence of a solvent. There is no particular limitation on the solvents and any solvents that do not affect the reaction adversely can be used.

Examples of the suitable inert solvent which can be used include water, lower alcohols such as methanol, ethanol, isopropanol, butanol and the like, aromatic hydrocarbons such as benzene, toluene, xylene and the like, ethers such as dioxane, tetrahydrofuran and the like, nitriles such as acetonitrile, propionitrile and the like, dimethyl sulfoxide, dimethylformamide, hexamethylphosphoric triamide and the like.

In the above reaction, the proportion of the compound of the formula (III) to the compound of the formula (II) is not particularly limited, and can be varied broadly. Usually the reaction is carried out using at least an equimolar amount, and preferably from 1.5 to 3 moles, of the compound of the formula (III) per mole of the compound of the formula (II).

Further, the reaction can be carried out in the presence of a basic compound which is used conventionally as a dehydrohalogenating agent.

Examples of suitable basic compound include inorganic basic compounds, for example, metal carbonates or hydrogencarbonates such as sodium carbonate, potassium carbonate, sodium hydrogencarbonate and the like, organic basic compounds such as triethylamine, pyridine, N,N-dimethylaniline and the like.

The reaction can be carried out usually at a temperature of from about room temperature to 150° C. and completed generally in about 1 to 10 hours.

Of the compounds of the formula (I), those in which the bonding between the 3- and 4-positions of the carbostyril nucleus is a single bond (i.e., compounds of the formula (Ia)) and those in which such bonding is a double bond (i.e., compounds of the formula (Ib)) can be converted to each other by reduction reaction or dehydrogenation reaction as shown in Reaction Scheme-2 below.

catalytic reductions. Examples of the catalyst which can be used include metals such as palladium, palladium black, palladium-carbon, platinum, platinum oxide, platinum black, Raney nickel, etc., in catalytic amounts usually used.

As for the solvent there can be used, for example, water, methanol, ethanol, isopropanol, dioxane, THF, hexane, cyclohexane, ethyl acetate, acetic acid, etc.

The reduction reaction can be carried out either at atmospheric pressure or under pressure. Usually, the reaction is carried out at about 0° to 100° C., preferably Reaction Scheme-2

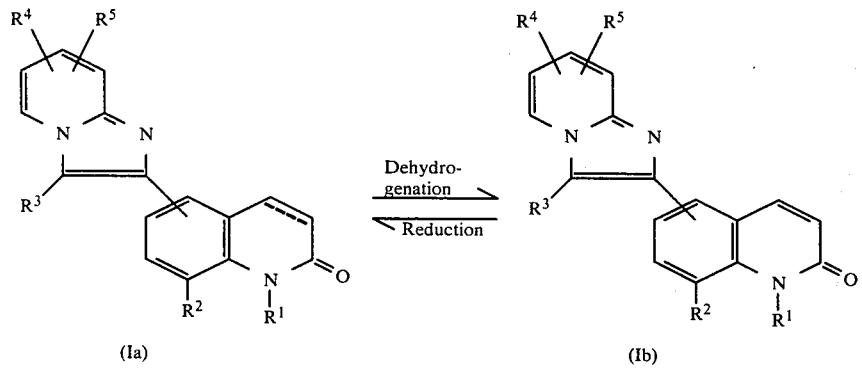

In the above formulae, $R^1$, $R^2$, $R^3$, $R^4$ and $R^5$ have the same meanings as defined above.

Dehydrogenation reaction of the compound of the formula (Ia) can be carried out in an appropriate solvent using a dehydrogenating agent. Examples of suitable dehydrogenating agent include benzoquinones such as 2,3-dichloro-5,6-dicyanobenzoquinone, chloranil (2,3,5,6-tetrachlorobenzoquinone), etc., halogenating agents such as N-bromosuccinimide, N-chlorosuccinimide, bromine, etc., dehydrogenating agents such as sulfur, selenium dioxide, etc., dehydrogenation metal catalysts such as palladium-carbon, palladium black, platinum black, palladium oxide, Raney nickel, etc.

When benzoquinones and halogenating agents are used as a dehydrogenating agent, the amount of the dehydrogenating agent which is used is not limited particularly and can be varied widely. Usually, 1 to 5 moles, preferably 1 to 2 moles, of the dehydrogenating agent per mole of the compound of the formula (Ia) is used. When the dehydrogenating metal catalysts are used, they are used in ordinary catalytic amounts. For example, the catalysts are used in about the same weight as the compound of the formula (Ia) to be used.

Examples of suitable solvent include water, ketones such as acetone, etc., ethers such as dioxane, tetrahydrofuran, methoxyethanol, dimethoxyethane, etc., aromatic hydrocarbons such as benzene, toluene, xylene, phenetole, tetralin, cumene, chlorobenzene, etc., halogenated hydrocarbons such as dichloromethane, dichloroethane, chloroform, carbon tetrachloride, etc., alcohols such as methanol, ethanol, isopropanol, butanol, tert-butanol, amyl alcohol, hexanol, etc., protic polar solvents such as acetic acid, etc., aprotic polar solvents such as DMF, DMSO, hexamethylphosphoric triamide, etc., and the like.

The reaction can be carried out usually at room temperature to 300° C., preferably at room temperature to 200° C. and completed generally in about 1 to 40 hours.

Reduction reaction of the compounds of the formula (Ib) can proceed under conventional conditions for room temperature to 70° C., and at atmospheric to 10 kg/cm$^2$, preferably atmospheric to 5 kg/cm$^2$.

Reaction Scheme-3

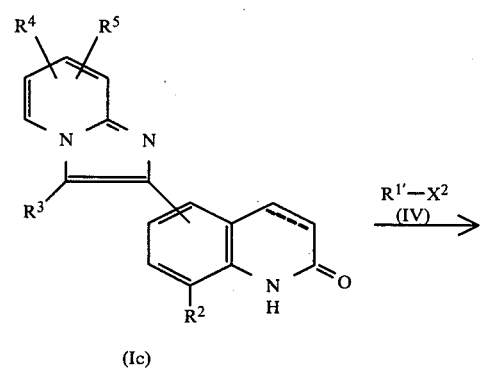

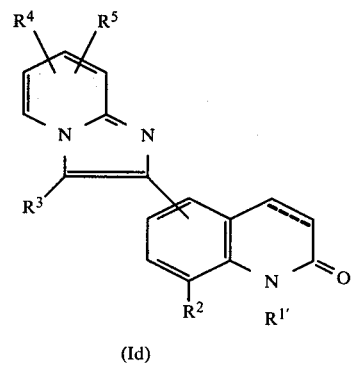

In the above formulae, $R^{1'}$ represents a lower alkyl group, a lower alkenyl group, a lower alkynyl group or a phenyl-lower alkyl group, $X^2$ represents a halogen atom, and $R^2$, $R^3$, $R^4$ and $R^5$ have the same meanings as defined above.

According to Reaction Scheme-3, in the case where the groups represented by $R^2$, $R^3$, $R^4$ and $R^5$ are each an inert group, a compound of the formula (I) in which $R^1$ represents a hydrogen atom or a compound of the formula (Ic) can be converted to a corresponding compound of the formula (I) in which $R^1$ represents a lower alkyl group, a lower alkenyl group, a lower alkynyl group or a phenyl-lower alkyl group or a compound of the formula (Id).

More particularly, a compound of the formula (Ic) can be reacted with a basic compound, for example, sodium hydride, potassium hydride, sodium amide, potassium amide, alkali metals such as sodium metal, potassium metal, etc., to convert the compound of the formula (Ic) to its alkali metal salt in which the nitrogen atom at the 1-position of the carbostyril nucleus takes part in salt formation. This reaction can be carried out in an appropriate solvent, for example, aromatic hydrocarbons such as benzene, toluene, xylene, etc., saturated hydrocarbons such as n-hexane, cyclohexane, etc., ethers such as diethyl ether, diethylene glycol dimethyl ether, 1,2-dimethoxyethane, dioxane, etc., aprotic polar solvents such as dimethylformamide, hexamethylphosphoric triamide, dimethyl sulfoxide, etc., with aprotic polar solvents being preferred.

The reaction can be carried out at a temperature of 0° to 200° C., preferably room temperature to 50° C.

The alkali metal salt of the compound of the formula (Ic) thus obtained can be reacted with a halide of the formula (IV) in a conventional manner. This reaction can proceed advantageously in an appropriate solvent which can be used in converting a compound of the formula (Ic) to its alkali metal salt, usually, at a temperature of about 0° to 70° C., preferably 0° C. to room temperature.

Proportion of the basic compound to be used to the compound of the formula (Ic) is usually 1 to 5 moles, preferably 1 to 3 moles, of the basic compound per mole of the compound of the formula (Ic). On the other hand, proportion of the halide of the compound of the formula (IV) to be used to the compound of the formula (Ic) is usually 1 to 5 moles, preferably 1 to 3 moles, of the halide of the formula (IV) per mole of the compound of the formula (Ic). The reaction can be completed in about 0.5 to 15 hours.

The carbostyril compounds of the formula (II) which can be used as a starting compound in Reaction Scheme-1 can readily be prepared in various processes. For example, they can be prepared according to processes shown in Reaction Schemes-4, -5, -6 and -7 below.

Of the compounds of the formula (II), those in which $R^2$ represents a hydroxy group or a lower alkoxy group can be prepared according to Reaction Scheme-4 below.

Reaction Scheme-4

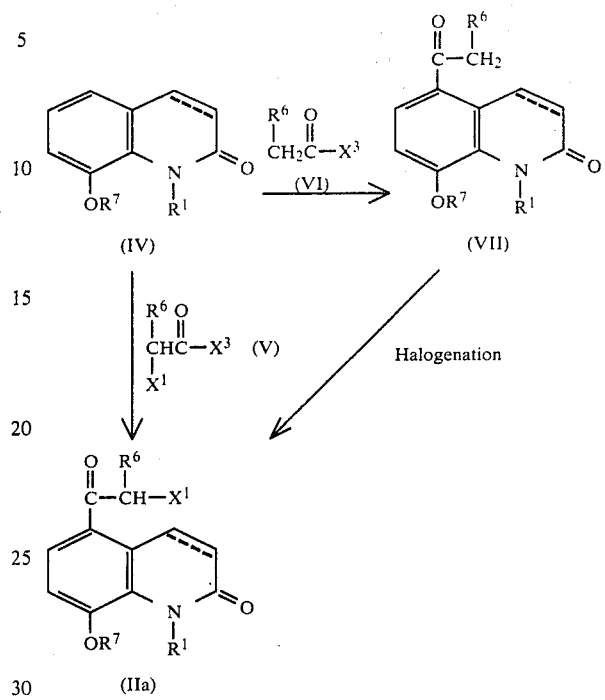

In the above formulae, $R^1$, $R^6$, $X^1$ and the bonding between the 3- and 4-positions of the carbostyril nucleus have the same meanings as defined above, $X^3$ represents a halogen atom, and $R^7$ represents a hydrogen atom or a lower alkyl group.

In Reaction Scheme-4 above, reaction between the carbostyril derivative of the formula (IV) and the halogenoalkanoyl halide derivative of the formula (V) can be carried out usually in the presence of a Lewis acid as a catalyst.

In the above reaction, any conventionally used Lewis acid can be used advantageously, for example, aluminum chloride, iron chloride, zinc chloride, tin chloride, etc.

The reaction can be carried out either in the absence of solvents or in the presence of an appropriate inert solvent, for example, carbon disulfide, methylene chloride, 1,2-dichloroethane, chlorobenzene, nitrobenzene, diethyl ether, dioxane, etc.

The reaction can be carried out usually at about room temperature to 150° C., preferably room temperature to 100° C.

Proportion of the compound of the formula (V) to the compound of the formula (IV) is usually equimolar amount to a large excess amount, preferably 2 to 6.5 moles, of the compound of the formula (V) per mole of the compound of the formula (IV).

Alternatively, a compound of the formula (IIa) can be prepared by reacting a compound of the formula (IV) with a compound of the formula (VI) instead of a compound of the formula (V) to form a compound of the formula (VII) and then halogenating this compound.

In the reaction between the compound of the formula (IV) and the compound of the formula (VI) the same reaction conditions as those under which the compound of the formula (IV) and the compound of the formula (V) are reacted can be employed.

the reaction a radical reaction initiator such as benzoyl peroxide, hydrogen peroxide, etc., may be used.

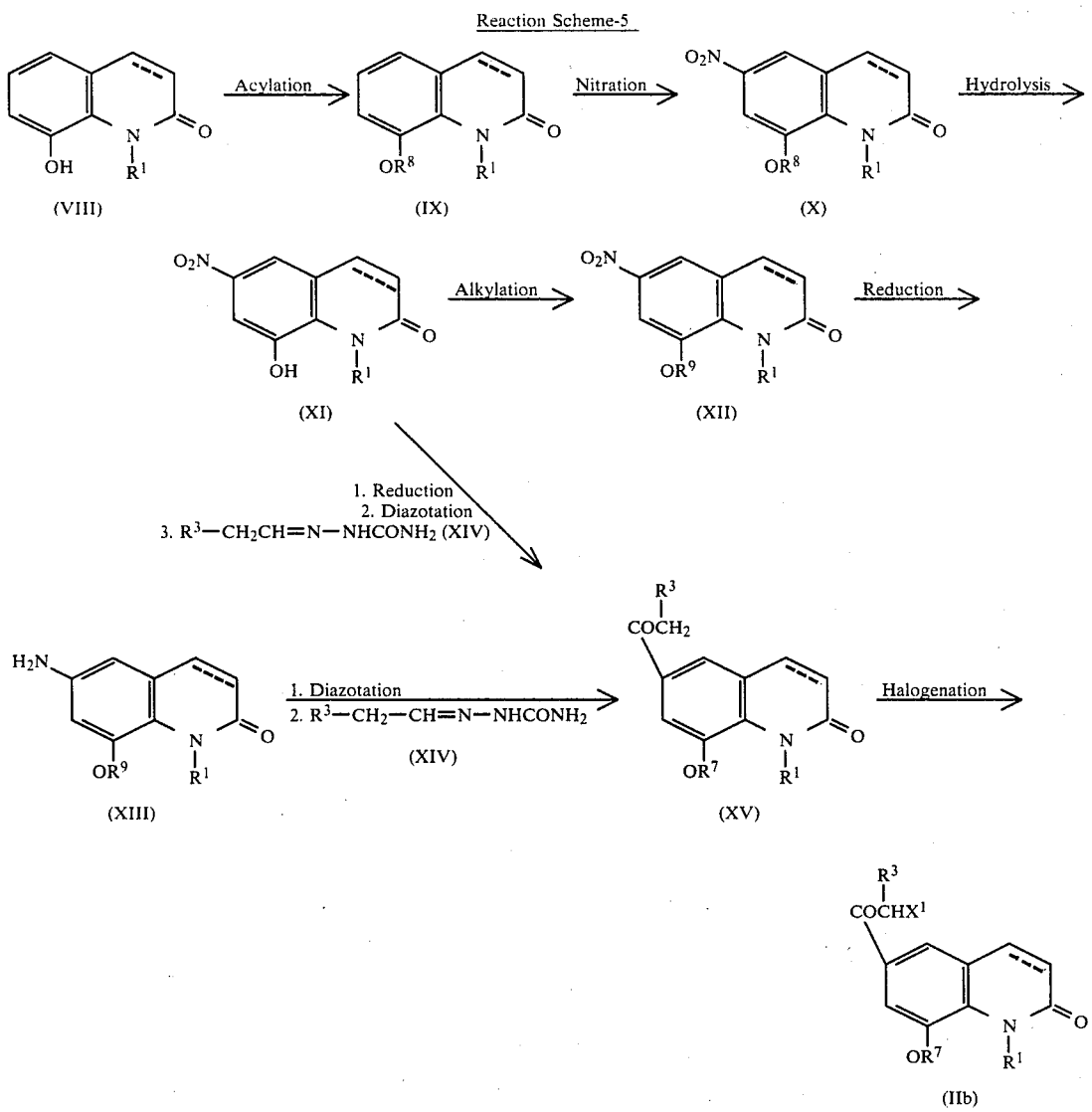

Reaction Scheme-5

Halogenation of the compound of the formula (VII) can be carried out in the presence of a halogenating agent conventionally used. In the reaction various known halogenating agents can be used. For example, there can be illustrated halogens such as bromine, chlorine, etc., N-halogenosuccinimides such as N-bromosuccinimide, N-chlorosuccinimide, etc.

Proportion of the halogenating agent to the compound of the formula (VII) is usually about 1 to 10 moles, preferably 1 to 5 moles, of the halogenating agent per mole of the compound of the formula (VII).

Examples of the solvents which can be used in the halogenation reaction of the compound of the formula (VII) include halogenated hydrocarbons such as dichloromethane, dichloroethane, chloroform, carbon tetrachloride, etc., organic acids such as acetic acid, propionic acid, etc., and the like.

The reaction can readily proceed usually under ice cooling or at a temperature up to the boiling point of the solvent used, preferably room temperature to 40° C. and can be completed generally in about 1 to 10 hours. In In the above formulae, $R^8$ represents a lower alkanoyl group, $R^9$ represents a lower alkyl group, $R^1$, $R^3$, $R^7$, $X^1$ and the bonding between the 3- and 4-positions of the carbostyril nucleus have the same meanings as defined above.

Acylation reaction of the compound of the formula (VIII) can be carried out by reacting the compound of the formula (VIII) with a lower alkanoic anhydride or its acid halide without solvent or in a solvent such as pyridine, benzene, nitrobenzene, ether, acetone, dioxane, etc., in the presence of a basic compound, e.g., alkali metal carbonates such as sodium carbonate, potassium carbonate, etc., organic bases such as triethylamine, N,N-dimethylaniline, 1,5-diazabicyclo[5,4,0]undecene-5 (DBU), etc., or an acidic compound such as sulfuric acid, p-toluenesulfonic acid, etc.

Proportion of the lower alkanoic anhydride or its acid halide to be used to the compound of the formula (VIII) is usually at least 1 mole to a large excess amount, preferably 1 to 10 moles, of the anhydride or halide per mole of the compound of the formula (VIII).

The acylation reaction can proceed usually at a temperature of from about −10° C. to 150° C., preferably 0° to 100° C. and be completed generally in about 10 minutes to 10 hours.

Nitration reaction of the compound of the formula (IX) can be carried out without solvent or in a solvent such as acetic acid, acetic anhydride, sulfuric acid, etc., in the presence of a nitration agent such as fuming nitric acid, concentrated nitric acid, a mixed acid (a mixture of sulfuric acid, fuming sulfuric acid, phosphoric acid or acetic anhydride and nitric acid), a combination of an alkali metal nitrate and sulfuric acid, a mixed acid anhydride of an organic acid with nitric acid such as acetyl nitrate, benzoyl nitrate, etc., a combination of nitrogen pentoxide or nitric acid and silver nitrate, a combination of acetone cyanohydrin nitrate or alkyl nitrate and sulfuric acid or polyphosphoric acid, and the like. The amount of nitration agent to be used is usually 1 to 1.5 moles per mole of the compound of the formula (IX).

The reaction can proceed usually at about −10° to 50° C. and can be completed generally in about 1 to 10 hours.

Hydrolysis reaction of the compound of the formula (X) can be carried out in the absence of solvents or in a suitable solvent such as water, methanol, ethanol, isopropanol, acetic acid using an acid or an alkali. Examples of suitable acid include hydrochloric acid, sulfuric acid, etc., and examples of alkali include potassium hydroxide, sodium hydroxide, potassium carbonate, sodium carbonate, sodium hydrogencarbonate, etc. The amounts of the acid and alkali are at least 1 mole per mole of the compound of the formula (X), respectively. Usually, they are used in a large excess amount relative to the compound of the formula (X). The reaction can be carried out usually at a temperature of about room temperature to 100° C. and completed generally in about 0.5 to 5 hours.

Alkylation reaction of the compound of the formula (XI) can be carried out in the presence of a basic compound using a conventional alkylating agent. Examples of suitable basic compound include alkali metals such as sodium metal, potassium metal, etc., and hydroxides, carbonates, bicarbonates and alcoholates thereof, and amines such as pyridine, piperidine, etc. As for the alkylating agent, there can be illustrated alkyl halides such as alkyl iodide (e.g., methyl iodide, etc.), alkyl chloride, alkyl bromide (e.g., methyl bromide, etc.), etc., dialkyl sulfates such as dimethyl sulfate, diethyl sulfate, etc., and the like.

The reaction can proceed advantageously in a suitable solvent. Examples of suitable solvent include water, lower alcohols such as methanol, ethanol, isopropanol, n-butanol, etc., ketones such as acetone; methyl ethyl ketone, etc., and the like.

The alkylating agent is used usually in from at least equimolar amount to a large excess amount, preferably 1 to 2 moles per mole of the compound of the formula (XI).

The reaction can proceed with ease at a temperature of from about room temperature to the boiling point of the solvent to be used. Generally, it can be carried out with heating.

Reduction reaction of the compound of the formula (XII) or (XI) can be carried out with ease by subjecting the compound of the formula (XII) or (XI) to catalytic reduction in a solvent such as water, acetic acid, methanol, ethanol, diethyl ether, dioxane, etc., in the presence of a catalyst such as palladium black, palladium-carbon, platinum oxide, platinum black, Raney nickel, etc., usually at room temperature under atmospheric pressure, or using a combination of iron, zinc, tin or stannous chloride and an acid (e.g., formic acid, acetic acid, hydrochloric acid, phosphoric acid, sulfuric acid, etc.), a combination of iron, ferrous sulfate, zinc or tin and an alkali (e.g., alkali metal hydroxides, alkali metal carbonates, ammonia, etc.), sulfates, sodium dithionite, sulfites, etc.

Diazotation reaction of the compound of the formula (XIII) or reduction product of the compound of the formula (XI) can be carried out in an aqueous solution using sodium nitrite and hydrochloric acid or sulfuric acid at a temperature of from about −30° C. to room temperature for about 1 to 3 hours.

The diazonium salt of the compound of the formula (XI) or (XIII) can further be reacted with a compound of the formula (XIV) to form a compound of the formula (XV). The amount of the compound of the formula (XIV) to be used is usually about 1 to 5 moles, preferably 1 to 2 moles, per mole of the diazonium salt.

The reaction can be carried out advantageously in the presence of a buffering agent such as sodium acetate, sodium carbonate, calcium carbonate, etc., and sodium sulfite and copper sulfate as a catalyst usually at 0° to 40° C. for about 1 to 5 hours.

Halogenation reaction of the compound of the formula (XV) can be carried out using a halogenating agent such as halogens, e.g., bromine, chlorine, etc., or N-halogenosuccinimides, e.g., N-bromosuccinimide, N-chlorosuccinimide, etc.

Proportion of the halogenating agent to the compound of the formula (XV) is usually 1 to 10 moles, preferably 1 to 5 moles, of the halogenating agent per mole of the compound of the formula (XV).

Examples of suitable solvent which can be used in the reaction include halogenated alkanes such as dichloromethane, dichloroethane, chloroform, carbon tetrachloride, etc.

The reaction can proceed with ease under ice cooling or at a temperature of up to the boiling point of the solvent used, preferably at room temperature to 40° C. and can be continued usually for about 1 to 10 hours. In the reaction, radical reaction initiator such as peroxides, e.g., benzoyl peroxide, hydrogen peroxide, etc., may be used.

Alternatively, after the diazotation of the compound of the formula (XI) or (XIII), a compound of the following formula

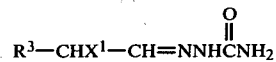

$$R^3-CHX^1-CH=NNHCNH_2$$

wherein $R^3$ and $X^1$ have the same meanings as defined above, may be used instead of the compound of the formula (XIV), whereby the compound of the formula (IIb) can be prepared from the compound of the formula (XIII) directly. In this case, the same reaction conditions under which the reaction using the compound of the formula is carried out can be used.

Of the compounds of the formula (XV) or (IIb), those in which $R^7$ represents a hydrogen atom can be prepared by heating the compound of the formula (XV) or (IIb) in which $R^7$ represents a lower alkyl group in a solvent such as water or dioxane in the presence of an acidic catalyst such as hydrobromic acid at 80° to 130° C. for 30 minutes to 6 hours.

Further, of the compounds of the formula (II), those in which R² represents a hydrogen atom, a lower alkyl group or a halogen atom can be prepared according to Reaction Scheme-6 below.

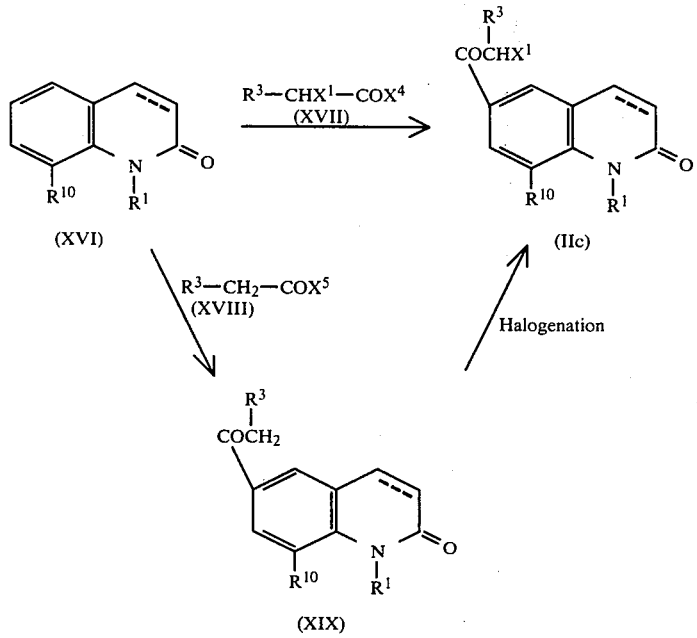

In the above formulae, R¹⁰ represents a hydrogen atom, a lower alkyl group or a halogen atom, X⁴ represents a halogen atom, a hydroxy group or a group of the formula $$-\overset{O}{\underset{\|}{O C}}-X^1 CH-R^3,$$ X⁵ represents a halogen atom, a hydroxy group, or a group of the formula $-\overset{O}{\underset{\|}{O C}}CH_2R^3$, R¹, R³, X¹ and the bonding between the 3- and 4-positions of the carbostyril nucleus have the same meanings as defined above.

The reaction between the compound of the formula (XVI) and the compound of the formula (XVII) and that between the compound of the formula (XVI) and the compound of the formula (XVIII) are called Friedel Crafts reaction, which can be carried out in a solvent in the presence of a Lewis acid.

Examples of suitable solvent include carbon disulfide, nitrobenzene, chlorobenzene, dichloromethane, dichloroethane, trichloroethane, tetrachloroethane, etc. As for the Lewis acid, any conventionally used Lewis acids can be employed. For example, aluminum chloride, zinc chloride, iron chloride, tin chloride, boron tribromide, boron trifluoride, concentrated sulfuric acid, etc., can be used.

The amount of Lewis acid to be used is not particularly limited and can be varied broadly. Usually, about 2 to 6 moles, preferably 3 to 4 moles, of Lewis acid per mole of the compound of the formula (XVI) can be used.

The compound of the formula (XVII) and the compound of the formula (XVIII) each can be used in an amount of usually at least 1 mole, preferably 1 to 2 moles, per mole of the compound of the formula (XVI).

The reaction temperature can be selected appropriately depending on other conditions. Usually, the reaction is carried out at about 0° to 120° C., preferably 20° to 70° C. The reaction time is varied broadly depending upon starting materials, catalysts, reaction temperatures and the like conditions. Usually, the reaction is completed in about 0.5 to 6 hours.

Halogenation reaction of the compound of the formula (XIX) can be carried out under the same conditions as those under which the halogenation of the compound of the formula (XV) is carried out.

Further, of the compounds of the formula (I), those in which R³ represents a halogen atom, a nitroso group, an amino group, a lower alkylamino group, an N,N-di-lower alkylamino group, a lower alkanoylamino group, an N,N-di-lower alkylaminomethyl group, a carbamoylmethyl group, a cyanomethyl group or a carboxymethyl group can be prepared from the compound of the formula (IA) in which R⁶ represents a hydrogen atom (ie., compound of the formula (Ie)) according to Reaction Schemes-7 to -11 below.

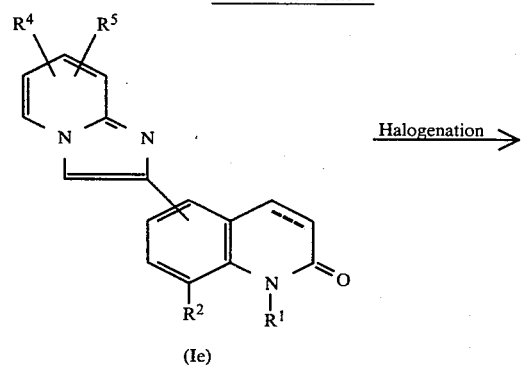

-continued
Reaction Scheme-7

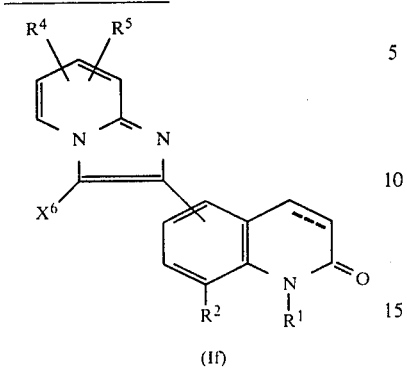

(If)

In the above formulae, $R^1$, $R^2$, $R^4$, $R^5$ and the bonding between the 3- and 4-positions of the carbostyril nucleus have the same meanings as defined above and $X^6$ represents a halogen atom.

According to Reaction Scheme-7, the compound of the formula (If) can be prepared by halogenating the compound of the formula (Ie) in a conventional solvent in the presence of a halogenating agent. In the reaction, any conventional halogenating agent can be used. For example, halogens such as chlorine, bromine, iodine, fluorine, etc., phosphorus oxychloride, phosphorus oxybromide, phosphorus pentachloride, phosphorus pentabromide, phosphorus trichloride, thionyl chloride, etc., and the like halogenating agents can be used.

Proportion of the halogenating agent to the compound of the formula (Ie) is not limited particularly and can be varied broadly. Usually, 1 to 10 moles, preferably 1 to 1.5 moles, of the halogenating agent per mole of the compound of the formula (Ie) can be used.

Examples of suitable inert solvent include halogenated hydrocarbons such as chloroform, dichloromethane, 1,2-dichloroethane, etc., ethers such as diethyl ether, dioxane, etc., organic acids such as acetic acid, propionic acid, etc., and the like.

The halogenation reaction can be carried out under ice cooling or at a temperature of about 0° to 100° C., preferably room temperature to 50° C. for about 1 to 12 hours.

Reaction Scheme-8

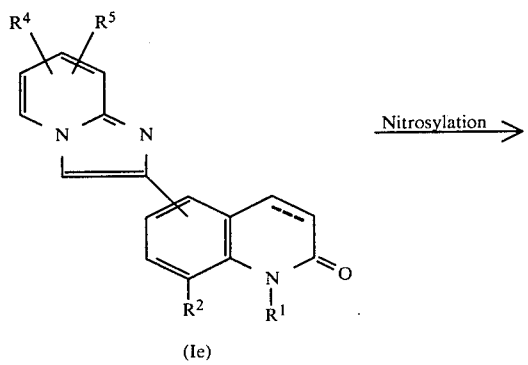

(Ie)

-continued
Reaction Scheme-8

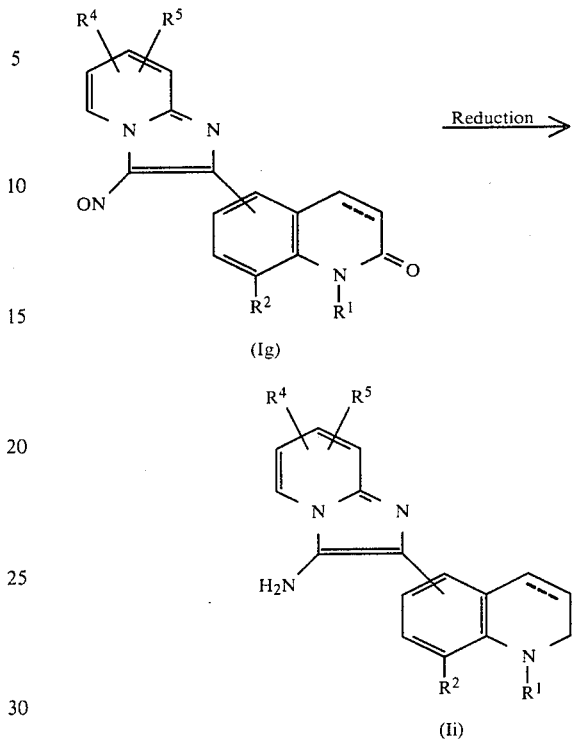

(Ig)

(Ii)

In the above formulae, $R^1$, $R^2$, $R^4$, $R^5$ and the bonding between the 3- and 4-positions of the carbostyril nucleus have the same meanings as defined above.

According to Reaction Scheme-8, of the compounds of the formula (I) in which $R^3$ represents a nitroso group (i.e., compound of the formula (Ig)) can be obtained by nitrosylation of the compound of the formula (Ie).

The reaction can be carried out in the absence of solvents or in a suitable inert solvent using a nitrosylating agent and an acid. Any conventional nitrosylating agents can be used. Among them, nitrites such as sodium nitrile, potassium nitrite, etc., are preferred. The proportion of the nitrosylating agent to the compound of the formula (Ie) is usually 1 to 2 moles, preferably 1 to 1.2 moles, of the nitrosylating agent per mole of the compound of the formula (Ie).

Examples of suitable acid include hydrochloric acid, sulfuric acid, phosphoric acid, acetic acid, propionic acid, butyric acid, isobutyric acid and the like conventional acids of which mineral acids are preferred. The acid can be used usually in excess amounts relative to the compound of the formula (Ie) when the reaction is carried out in the absence of solvents. On the other hand, the amount of the acid can be varied broadly and usually is at least 1 mole per mole of the compound of the formula (Ie) when the reaction proceeds in a solvent.

As for the solvent there can be illustrated conventional inert solvents such as water, lower fatty acids, e.g., acetic acid, propionic acid, butyric acid, isobutyric acid, etc., lower fatty acid anhydrides, e.g., acetic anhydride, propionic anhydride, butyric anhydride, isobutyric anhydride, etc., ethers, e.g., dioxane, tetrahydrofuran, etc., dimethylformamide, dimethyl sulfoxide, and the like.

The reaction can be carried out usually at about 30° to 100° C., preferably 0° to 50° C. and completed for about 30 minutes to 3 hours.

Reduction of the compound of the formula (Ig) thus formed gives rise to the compounds of the formula (I) in which $R^3$ represents an amino group (i.e., compound of the formula (Ii)).

This reduction reaction can be carried out using a conventional reducing agent, for example, a mixture of iron and hydrochloric acid, zinc and acetic acid, and tin or stannous chloride and hydrochloric acid in an amount of 1 mole to a large excess amount, preferably 3 to 5 moles, per mole of the compound of the formula (Ig).

Alternatively, the above reaction can be carried out using a suitable hydrogenating catalyst such as palladium black, palladium-carbon, Raney nickel, platinum dioxide, etc. The reaction can proceed advantageously in a solvent, for example, water, lower alcohols such as methanol, ethanol, isopropanol, etc., acetic acid and the like. Reaction conditions are not limited particularly and can be varied broadly depending on the kind and amount of the reducing agent or hydrogenating catalyst. Usually, the reaction is carried out at about 0° to 150° C., preferably 50° to 100° C. when a reducing agent is used and at about 0° to 100° C., preferably room temperature at atmospheric pressure of hydrogen gas when a hydrogenating catalyst is used.

sents a hydrogen atom or a lower alkyl group and $R^{12}$ represents a hydrogen atom or a methyl group.

According to Reaction Scheme-9 above, of the compounds of the formula (I), those in which $R^3$ represents a lower alkanoylamino group (i.e., compounds of the formula (Ij)) can be prepared by acylating the compound of the formula (I). In the reaction, various reaction conditions under which conventional acylation reactions proceed can be used. For example, the objective compound of the formula (Ij) can be obtained with ease by reacting the compound of the formula (Ii) with a lower alkanoic acid or its acid anhydride or halide.

The reaction can be carried out usually in the presence of a basic compound or an acidic compound. Examples of suitable basic compound include organic bases such as triethylamine, trimethylamine, pyridine, dimethylaniline, N-methylmorpholine, 1,5-diazabicyclo[4,3,0]-nonene-5 (DBN), 1,5-diazabicyclo[5,4,0]undecene-5 (DBU), 1,4-diazabicyclo[2,2,2]octane (DABCO), etc., inorganic bases such as potassium carbonate, sodium carbonate, potassium hydrogencarbonate, sodium hydrogencarbonate, etc. On the other hand, examples of suitable acidic compound include mineral acids such as sulfuric acid, hydrochloric acid, etc.

The above reaction can generally proceed in a solvent. Examples of suitable solvent include halogenated carbohydrates such as methylene chloride, chloroform, dichloroethane, etc., aromatic hydrocarbons such as Reaction Scheme-9

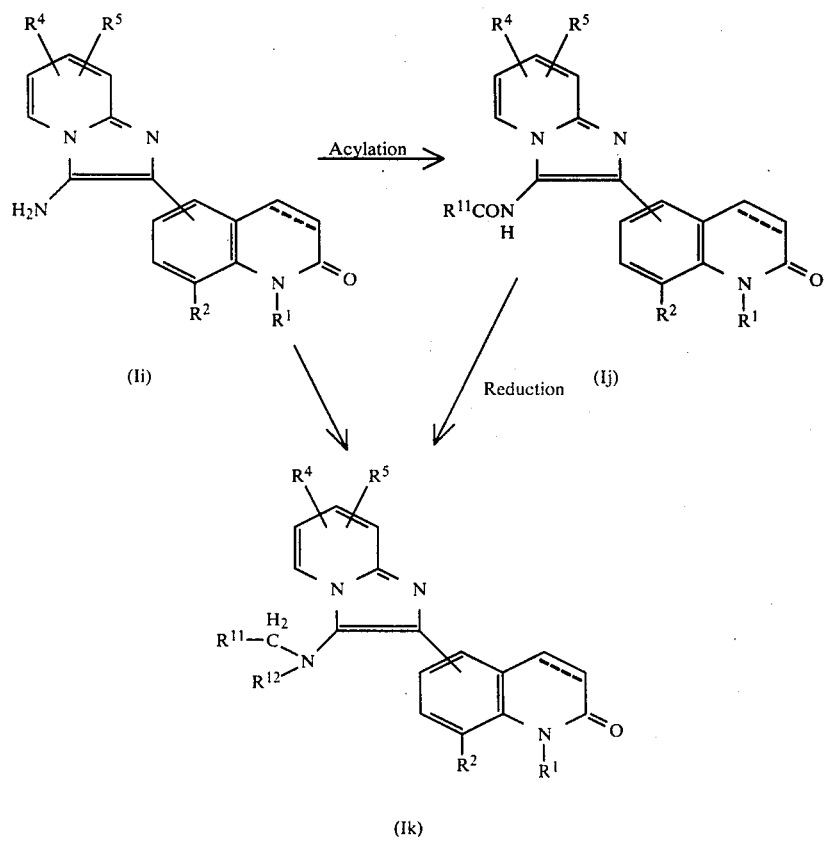

In the above formulae, $R^1$, $R^2$, $R^4$, $R^5$ and the bonding between the 3- and 4-positions of the carbostyril nucleus have the same meanings as defined above, $R^{11}$ reprebenzene, toluene, xylene, etc., ethers such as diethyl ether, tetrahydrofuran, dimethoxyethane, etc., esters such as methyl acetate, ethyl acetate, etc., and aprotic polar solvents such as N,N-dimethylformamide, dimethyl sulfoxide, hexamethylphosphoric triamide, etc.

In the above reaction, the amount of the lower alkanoic acid or its anhydride or halide is not limited particularly and can be varied broadly. Usually, 1 to 10 moles, preferably 1 to 2 moles, of the lower alkanoic acid or its anhydride or halide per mole of the compound of the formula (Ii) can be used. Further, there is no particular limitation on the reaction temperature and reaction time. Usually, the reaction can be carried out at a temperature of about −30° to 150° C., preferably 0° to 100° C., for about 30 minutes to 12 hours.

Of the compounds of the formula (Ik), those in which $R^{12}$ represents a hydrogen atom can be prepared by reducing the compound of the formula (Ij). The reduction reaction can be carried out under conventional conditions under which the carbonyl group in an amido bond is reduced to form a methylene group. For example, the reaction can proceed in the presence of lithium aluminum hydride, sodium borohydride or a like catalyst.

Of the compounds of the formula (Ik), those in which $R^{11}$ represents a hydrogen atom and $R^{12}$ represents a methyl group can be prepared by reducing a compound of the formula (Ii). In this reduction reaction can be applied Eschweiler-Clarke Reaction which can usually be carried out with ease by heating the compound of the formula (Ii) in the presence of formic acid and formalin in the absence of solvents.

Proportions of formic acid and formalin to the compound of the formula (Ii) are not limited particularly and can be varied broadly. Usually, formalin is used in an amount of about 1 to 5 moles, preferably 1 to 1.5 moles, per mole of the compound of the formula (Ii), while the amount of formic acid is about 1 to 10 moles, preferably 3 to 5 moles, per mole of the compound of the formula (Ii). There is no particular limitation on the reaction temperature and time and can be varied broadly. Usually, the reaction is carried out at about room temperature to 150° C., preferably 80° to 120° C. for about 3 to 30 hours.

Reaction Scheme-10

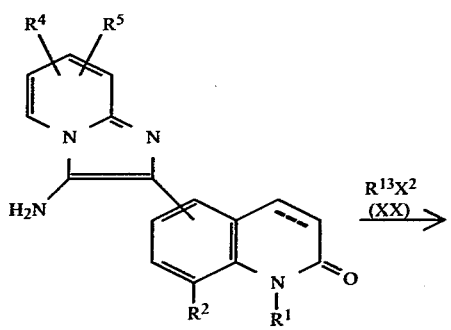

(Ii)

-continued
Reaction Scheme-10

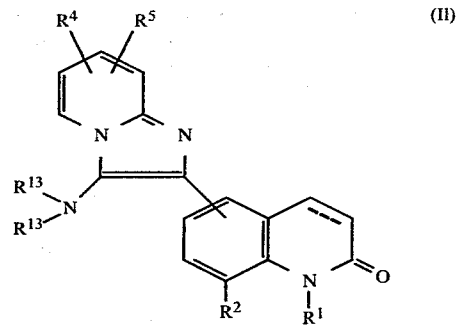

(II)

In the above formulae, $R^1$, $R^2$, $R^4$, $R^5$, $X^2$ and the bonding between the 3- and 4-positions of the carbostyril nucleus have the same meanings as defined above, and $R^{13}$ represents a lower alkyl group.

Of the compounds of the formula (I), those in which $R^3$ represents an N,N-di-lower alkylamino group (i.e., compound of the formula (II) can be prepared by reacting the compound of the formula (Ii) with a compound of the formula (XX). The reaction can be carried out in the presence of a dehalogenating agent.

As for the dehalogenating agent, various conventional basic compounds can be used. Representative examples of the basic compound include organic bases such as sodium hydroxide, potassium hydroxide, sodium carbonate, potassium hydrogencarbonate, etc., alkali metals such as sodium metal, potassium metal, etc., organic bases such as triethylamine, pyridine, N,N-dimethylaniline, etc.

The reaction can proceed either in the absence of solvents or in the presence of a solvent. Any solvents that do not take part in the reaction can be used. For example, alcohols such as methanol, ethanol, propanol, etc., ethers such as diethyl ether, tetrahydrofuran, dioxane, ethylene glycol monomethyl ether, etc., aromatic hydrocarbons such as benzene, toluene, xylene, chlorobenzene, etc., ketones such as acetone, methyl ethyl ketone, etc., aprotic polar solvents such as N,N-dimethylformamide, dimethyl sulfoxide, hexamethylphosphoric triamide, etc., and the like solvents can be used advantageously.

Proportion of the compound of the formula (XX) to the compound of the formula (Ii) is usually at least 2 moles, preferably 2 to 4 moles, of the compound of the formula (XX) per mole of the compound of the formula (Ii).

When using about 1 mole of the compound of the formula (XX) per mole of the compound of the formula (Ii), a compound of the formula (I) in which $R^3$ represents a mono-lower alkylamino group can be prepared. This compound can further be reacted with a compound of the formula $$R^{13'}X^2$$

wherein $R^{13'}$ represents a lower alkyl group and $X^2$ has the same meaning as above, to form a compound of the formula (I) in which $R^3$ represents an N,N-dialkylamino group the alkyl groups of which are different from each other.

The reaction can be carried out usually at about −30° to 100° C., preferably 0° to 50° C. and completed generally in about 30 minutes to 12 hours.

Reaction Scheme-11

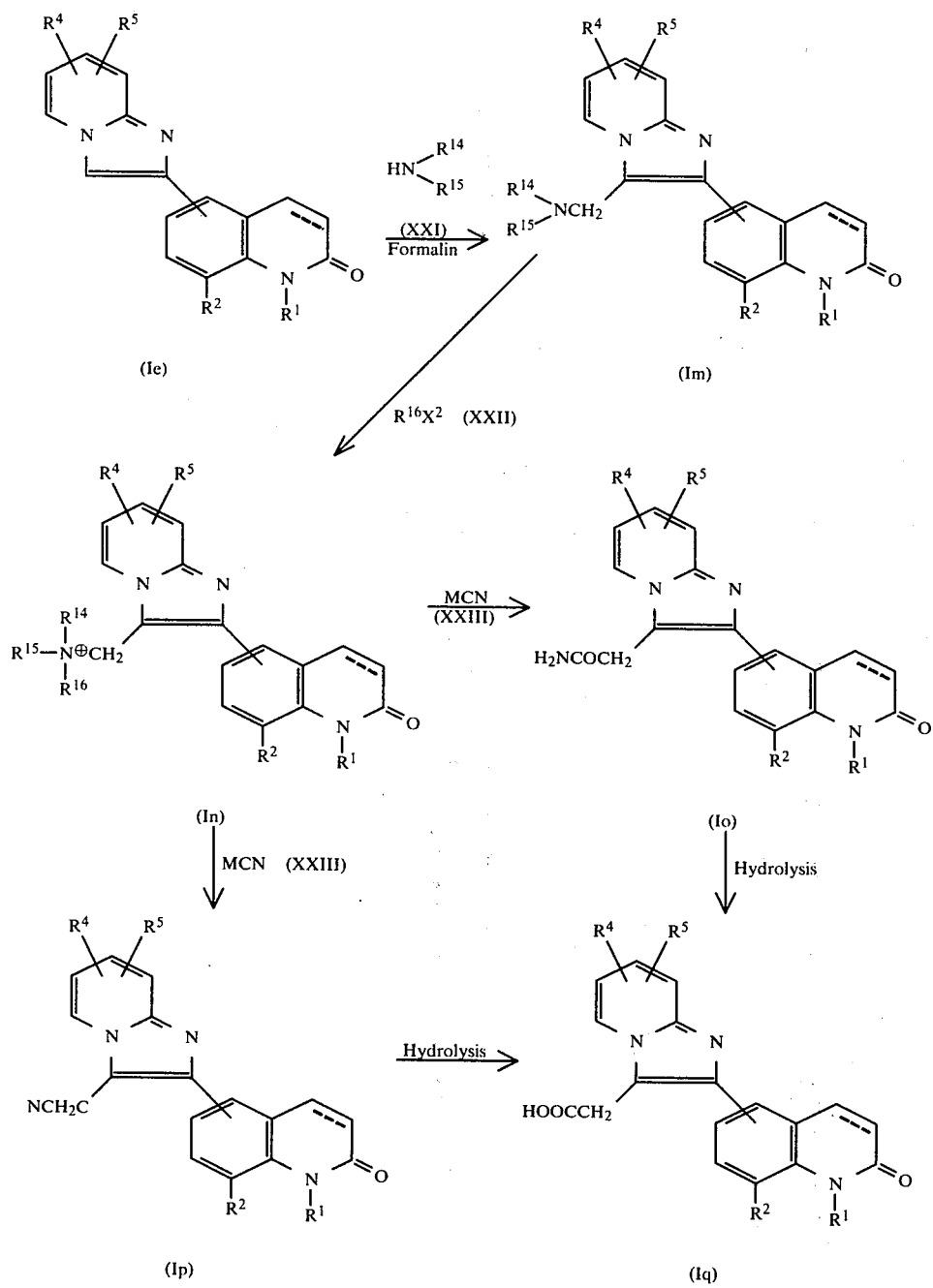

In the above formulae, $R^1$, $R^2$, $R^4$, $R^5$, $X^2$ and the bonding between the 3- and 4-positions of the carbostyril nucleus have the same meanings as defined above, $R^{14}$, $R^{15}$ and $R^{16}$, which may be the same or different, each represents a lower alkyl group and M represents an alkali metal.

According to Reaction Scheme-11, of the compounds of the formula (I), those in which $R^3$ represents an N,N-di-lower alkylaminomethyl group (i.e., compound of the formula (Im)) can be prepared by reacting a compound of the formula (Ie) with a di-lower alkylamine of the formula (XXI) and formalin.

The reaction can be carried out either in the absence of solvents or in the presence of a solvent. As for the solvent any solvents that do not take part in the reaction can be used. For example, water, lower alcohols such as methanol, ethanol, isopropanol, etc., lower fatty acids such as acetic acid, propionic acid, etc., and the like solvents can be used.

Proportions of the compound of the formula (XXI) and formalin to the compound of the formula (Ie) each is usually about 1 to 3 moles, preferably 1 mole, of the compound of the formula (XXI) or formalin per mole of the compound of the formula (Ie).

The reaction can be carried out usually at about 0° to 150° C., preferably room temperature to 100° C. and completed generally in about 3 to 6 hours.

Further, tertiary ammonium salt of the formula (In) can be prepared by reacting the compound of the formula (Im) thus obtained with a compound of the formula (XXII). The reaction can be carried out either in the absence of solvents or in the presence of a solvent. Any solvents that do not take part in the reaction can be used. For example, water, lower alcohols such as methanol, ethanol, isopropanol, etc., halogenated hydrocarbons such as dichloromethane, chloroform, carbon tetrachloride, etc., acetonitrile, propionitrile, N,N-dimethylformamide, and the like solvents can be used.

Proportion of the compound of the formula (XXII) to the compound of the formula (Im) is usually 1 mole to a large excess amount, preferably 1 to 2 moles, of the compound of the formula (XXII) per mole of the compound of the formula (Im).

The reaction can be carried out usually at about 0° to 150° C., preferably 30° to 80° C. and completed generally in about 30 minutes to 4 hours.

Still further, of the compounds of the formula (I), those in which $R^3$ represents a carbamoylmethyl group (i.e., compound of the formula (Io)) or a cyano group (i.e., compound of the formula (Ip)) can be prepared by reacting the compound of the formula (In) with a compound of the formula (XXIII).

Each reaction can be carried out in an inert solvent, for example, water, lower alcohols such as methanol, ethanol, isopropanol, etc., nitriles such as acetonitrile, propionitrile, etc., and the like.

Preferred examples of the compound of the formula (XXIII) include potassium cyanide, sodium cyanide, etc.

In preparing the compound of the formula (Io), the compound of the formula (XXIII) is used usually in an equimolar to a large excess amount relative to the compound of the formula (In). Preferably, it is used in an amount of 3 to 4 moles per mole of the compound of the formula (In).

The reaction can be carried out usually at about room temperature to 150° C., preferably 60° to 100° C. for about 3 to 12 hours, preferably 5 to 6 hours.

On the other hand, in preparing the compound of the formula (Ip), usually about 1 to 2 moles, preferably 1 mole, of the compound of the formula (XXIII) is reacted with 1 mole of the compound of the formula (In) at about room temperature to 150° C., preferably 60° to 100° C. for about 30 minutes to 1 hour.

Moreover, of the compounds of the formula (I), those in which $R^3$ represents a carboxymethyl group (i.e., compound of the formula (Iq)) can be prepared by hydrolyzing the compound of the formula (Io) or (Ip). The hydrolysis reaction can be carried out in the absence of solvents or in a suitable solvent, for example, water, lower alcohols such as methanol, ethanol, isopropanol, etc., acetic acid and the like in the presence of an acid or an alkali. As for the acid there can be illustrated mineral acids such as hydrochloric acid, sulfuric acid, etc. Examples of the alkali include sodium hydroxide, potassium hydroxide, potassium carbonate, sodium carbonate, etc.

The acid or alkali can be used usually at least 1 mole per mole of the compound of the formula (Io) or (Ip). Usually, a large excess amount of the acid or alkali relative to the compound of the formula (Io) or (Ip) is used.

The reaction can be carried out usually at about room temperature to 150° C., preferably 50° to 100° C. and completed generally in about 30 minutes to 10 hours.

Further, of the compounds of the formula (I), those in which $R^2$ represents a hydroxy group can be prepared by hydrolyzing a compound of the formula (I) in which $R^2$ represents a lower alkoxy group under the same conditions as those under which the compound of the formula (XV) or (IIb) is hydrolyzed.

The compounds of this invention represented by the formula (I) prepared as described above can form pharmaceutically acceptable salts with acids and this invention also includes within its scope such pharmaceutically acceptable salts. The pharmaceutically acceptable acids which can be used for the salt formation can be various inorganic acids, for example, hydrochloric acid, sulfuric acid, phosphoric acid, hydrobromic acid, organic acids such as oxalic acid, maleic acid, fumaric acid, malic acid, tartaric acid, citric acid, benzoic acid and the like.

The compounds of the formula (I) can be converted into a corresponding salt when they have an acid group by reacting the acid group with a pharmaceutically acceptable basic compound. Examples of basic compounds are inorganic basic compounds such as sodium hydroxide, potassium hydroxide, calcium hydroxide, sodium carbonate, sodium hydrogencarbonate and the like.

As stated above, the salts of the compound of the formula (I) as used herein refers to acid addition salts thereof with pharmaceutically acceptable acids and basic compounds as well as quaternary ammonium salts thereof with halides such as lower alkyl halides.

The compounds of the formula (I) and the salts thereof obtained as described above can be isolated from the respective reaction mixtures upon completion of the reaction and purified by conventional procedures, for example, solvent extraction, dilution method, precipitation, recrystallization, column chromatography, preparative thin layer chromatography and the like.

As is apparent to those skilled in the art, the compounds of the formula (I) can exist in optically active forms and this invention includes such optical isomers within its scope.

In using the compounds of this invention of the formula (I) and the salts thereof as therapeutic agents, these compounds can be formulated into pharmaceutical compositions together with ordinary pharmaceutically acceptable carriers. Suitable carriers which can be used are, for example, solvents or excipients such as fillers, extenders, binders, wetting agents, disintegrants, surface active agents and lubricants which are usually employed to prepare such drugs depending on the type of dosage form.

Various dosage forms of the therapeutic agents as a cardiotonic agent can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogencarbonate, calcium carbonate, Tween, sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The amount of the compound of the formula (I) and the pharmaceutically acceptable salts thereof of this invention as an active ingredient to be incorporated into a pharmaceutical composition useful as a cardiotonic agent is not particularly limited, and can vary over a wide range. A suitable therapeutically effective amount of the compound of the general formula (I) and the pharmaceutically acceptable salts thereof of this invention is usually about 1 to about 70% by weight, preferably 5 to 50% by weight, based on the entire composition.

There is no particular restriction on the manner of using the cardiotonic agent, and it can be administered by routes suitable for the particular forms thereof. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the cardiotonic agent can be singly administered intramuscularly, intracutaneously, subcutaneously, or intraperitoneally. The suppository is administered intrarectally and the ointment is coated on the skin.

The dosage of the cardiotonic agent is suitably selected according to the purpose of use, the symptoms, etc. Usually, a preferred dosage of the compound of this invention is about 1 to 10 mg/kg body weight per day. It is advantageous that the active ingredient is contained in a single unit dose form in an amount of 50 to 250 mg.

This invention will be described in greater detail with reference to Reference Examples, Examples and Preparation Examples but is not limited thereto.

REFERENCE EXAMPLE 1

8-Hydroxy-3,4-dihydrocarbostyril (20 g) was suspended in acetic anhydride (100 ml). Sulfuric acid (5 drops) was added to the resulting suspension and the mixture was stirred at 80° C. for 1.5 hours. To the reaction mixture was added acetic acid (100 ml) and the mixture was ice-cooled, and a solution of 10.1 ml of concentrated nitric acid (d=1.38) in 30 ml of acetic anhydride was added thereto with stirring. The stirring was continued for one night at room temperature. The reaction mixture was poured into ice water to precipitate crystals, which were collected by filtration to give 21.74 g of 6-nitro-8-acetoxy-3,4-dihydrocarbostyril.

m.p. above 300° C., pale yellow powders
NMR (DMSO-$d_6$)

| $\delta$ (ppm) = | 8.03 (d, J = 2.5 Hz, 1H), |
| --- | --- |
| | 7.96 (d, J = 2.5 Hz, 1H), |
| | 3.20–2.98 (m, 2H), |
| | 2.68–2.45 (m, 2H), |
| | 2.33 (s, 3H) |

REFERENCE EXAMPLE 2

Hydrochloric acid (200 ml) was added to 6-nitro-8-acetoxy-3,4-dihydrocarbostyril (20 g) and the mixture was refluxed for 4 hours. After ice cooling, crystals which precipitated were collected by filtration and recrystallized from methanol to give 13.76 g of 6-nitro-8-hydroxy-3,4-dihydrocarbostyril.

m.p. 270° C., pale yellow scales

REFERENCE EXAMPLE 3

6-Nitro-8-hydroxy-3,4-dihydrocarbostyril (10 g) and potassium carbonate (13.3 g) were mixed with acetone (70 ml) and water (70 ml) and the mixture was refluxed with adding dropwise 12.1 g of dimethyl sulfate. After refluxing was continued for 4 hours, the reaction mixture was cooled, and crystals which precipitated were collected by filtration and washed with water to give 8.22 g of 6-nitro-8-methoxy-3,4-dihydrocarbostyril.

m.p. 230° C., yellow needles

REFERENCE EXAMPLE 4

6-Nitro-8-methoxy-3,4-dihydrocarbostyril (2 g) and 5% palladium-carbon (0.2 g) were added in ethanol (50 ml) and catalytic reduction was conducted at a hydrogen gas pressure of 3 kg/cm² for 1 hour. Then, the reaction mixture was filtered and the filtrate was concentrated. The residue was recrystallized from benzene to give 1.7 g of 6-amino-8-methoxy-3,4-dihydrocarbostyril.

m.p. 157°–158° C., colorless needles

REFERENCE EXAMPLE 5

To a mixture of 6-amino-8-methoxy-3,4-dihydrocarbostyril (12 g), concentrated hydrochloric acid (16 ml) and water (50 ml) was added ice (30 g), and sodium nitrite (5 g) and water (20 ml) were added gradually to the resulting mixture under ice-cooling. After completion of addition, the resulting mixture was reacted at 0° to 5° C. for 1 hour. On the other hand, a heated solution of acetaldehyde semicarbazide (10 g) in water (50 ml) and then sodium sulfite (0.25 g) and copper sulfate (3.2 g) were added to a solution of sodium acetate (34 g) in water (40 ml), and the internal bath was adjusted to a temperature of 10° to 20° C. The solution was stirred and below the surface of the solution was added gradually a solution prepared by adding a solution of sodium acetate (26 g) in water (46 ml) to the above diazonium salt solution. After stirring was continued for 2 hours, the reaction was allowed to stand for one night. Precipitates which formed were collected by filtration and washed with water. They were added in 200 ml of 2 N hydrochloric acid and the mixture was refluxed for 2 hours. After cooling, the reaction mixture was extracted with chloroform (150 ml) twice and the chloroform layer was washed with water. The solution was filtered through a short column charged with silica gel-activated carbon. This column was washed with 500 ml of chloroform. The two chloroform layers were combined and chloroform was evaporated. The residue was recrystallized from benzene to give 5.1 g of 6-acetyl-8-methoxy-3,4-dihydrocarbostyril.

m.p. 150° C., pale yellow needles

REFERENCE EXAMPLE 6

To a solution of 6-acetyl-8-methoxy-3,4-dihydrocarbostyril (3.1 g) in chloroform (30 ml) was added dropwise a solution of bromine (2.26 g) in chloroform (20 ml) with stirring at room temperature. After completion of addition, the mixture was stirred for 30 minutes at room temperature, thereafter, the reaction mixture was concentrated and the residue was recrystallized from methanol to give 3.2 g of 6-($\alpha$-bromoacetyl)-8-methoxy-3,4-dihydrocarbostyril.

m.p. 206°–207° C., colorless needles

REFERENCE EXAMPLE 7

To a solution of aluminum chloride (44 g) and $\alpha$-bromopropionyl chloride (43 g) in carbon disulfide (150 ml) was added portionwise 3,4-dihydrocarbostyril (8 g) while refluxing with stirring. After completion of addition, the mixture was refluxed with stirring for 2 hours. After cooling, the mixture was poured into ice water and crystals which precipitated were collected by filtration and washed with water. Recrystallization from ethanol gave 14.2 g of 6-($\alpha$-bromopropionyl)-3,4-dihydrocarbostyril.

m.p. 192°–193° C., pale yellow scales

REFERENCE EXAMPLE 8

To a solution of aluminum chloride (80 g) and chloroacetyl chloride (72 g) in carbon disulfide (200 ml) was added portionwise in 20 minutes a suspension of 3,4-dihydrocarbostyril (14.7 g) in carbon disulfide (100 ml) while refluxing with stirring. After completion of addition, the mixture was refluxed with stirring for 2 hours. After cooling, the reaction mixture was poured into ice water, and crystals which precipitated were collected by filtration, washed with water and recrystallized from ethanol to give 20 g of 6-chloroacetyl-3,4-dihydrocarbostyril.

m.p. 230°–231° C., colorless needles

REFERENCE EXAMPLE 9

In the same manner as in REFERENCE EXAMPLE 8 except that carbostyril was used in place of 3,4-dihydrocarbostyril, 6-chloroacetylcarbostyril was obtained.

m.p. 275°–277° C., pale green needles.

REFERENCE EXAMPLE 10

8-Methyl-3,4-dihydrocarbostyril (16.1 g) was suspended in carbon disulfide (100 ml) and $\alpha$-bromopropionyl bromide (35 g) was added to the suspension with stirring and cooling with ice water. Then, anhydrous alminum chloride (30 g) was added portionwise to the mixture followed by refluxing for 3 hours. Under reduced pressure carbon disulfide was evaporated and the residue was decomposed by the addition of ice water (500 ml).

Tarry product which precipitated was separated and washed with water. A small amount of methanol was added to the product to form crystals. The crystals were collected by filtration and recrystallized from methanol to give 14.3 g of 8-methyl-6-$\alpha$-bromopropionyl-3,4-dihydrocarbostyril.

m.p. 232.5°–233.5° C., colorless needles

REFERENCE EXAMPLE 11

To a solution of $\alpha$-bromopropionyl bromide (60 g) and aluminum chloride (40 g) in carbon disulfide (100 ml) was added 8-chloro-3,4-dihydrocarbostyril (10 g). After refluxing the mixture for 5 hours, carbon disulfide was evaporated and heated at 70° to 80° C. for 5 hours. The reaction mixture was poured into ice water and allowed to stand overnight. The mixture was extracted with chloroform and the chloroform layer was washed with water, dried and treated with activated carbon followed by evaporating chloroform. The residue was washed with diethyl ether and collected by filtration. The residue gave uniform crude crystals upon TLC. The crystals thus obtained were re-crystallized from methanol to give 12 g of 8-chloro-6-$\alpha$-bromopropionyl-3,4-dihydrocarbostyril.

m.p. 180°–182° C., pale yellow needles

REFERENCE EXAMPLES 12

To a solution of 8-hydroxycarbostyril (27 g) and chloroacetyl chloride (37 ml) in ntirobenzene (250 ml) was added aluminum chloride (85 g) portionwise and the mixture was stirred at 70° C. for 20 hours. After adding 10% hydrochloric acid (500 ml), nitrobenzene was removed by steam distillation. After cooling, crystals which formed were collected by filtration, washed with 300 ml of hot water and recrystallized from methanol to give 4.0 g of 5-chloroacetyl-8-hydroxycarbostyril.

m.p. 285°–287° C. (decomp.), pale yellow crystals

EXAMPLE 1

6-($\alpha$-Bromopropionyl)-1-methyl-3,4-dihydrocarbostyril (5 g), 2-aminopyridine (4.77 g) and acetonitrile (20 ml) were refluxed for 1.5 hours. The reaction mixture was cooled with ice water and crystals which precipitated were collected by filtration. The crystals were dissolved in acetone and the solution was adjusted to pH of about 1 by the addition of 48% hydrobromic acid. Crystals which formed were collected by filtration and recrystallized from water to give 5.68 g of 6-(3-methylimidazo[1,2-a]pyridine-2-yl)-1-methyl-3,4-dihydrocarbostyril monohydrobromide.

m.p. above 300° C., colorless powders
NMR (DMSO-d₆)

| δ (ppm) = 8.85 (d, J = 7 Hz, 1H) |
|---|
| 8.13–7.20 (m, 6H), |
| 3.33 (s, 3H) |
| 3.15–2.87 (m, 2H) |
| 2.73 (s, 3H) |
| 2.68–2.37 (m, 2H) |

EXAMPLE 2

8-Chloro-6-(α-bromopropionyl)-3,4-dihydrocarbostyril (4 g), 2-aminopyridine (3.57 g) and acetonitrile (20 ml) were refluxed for 3 hours. The reaction mixture was concentrated to dryness and the residue (oily product) was washed with water. Then, the residue was dissolved in acetone and 48% hydrobromic acid was added to the solution to adjust pH to about 1 and crystals which formed were crystallized by filtration. The crude crystals thus obtained were recrystallized from water to give 2.74 g of 8-chloro-6-(3-methylimidazo[1,2-a]-pyridine-2-yl)-3,4-dihydrocarbostyril monohydrobromide hemihydrate.

m.p. above 300° C., pale yellow powders
NMR (DMSO-d₆)

| δ (ppm) = 9.78 (s, 1H) |
|---|
| 8.83 (d, J = 7 Hz, 1H) |
| 8.03–7.43 (m, 5H) |
| 3.23–2.97 (m, 2H) |
| 2.74 (s, 3H) |
| 2.70–2.43 (m, 2H) |

EXAMPLE 3

In an analogous manner as in Example 2, the following compounds were prepared using appropriate starting materials.

8-Methyl-6-(3-methylimidazo[1,2-a]pyridine-2-yl)-3,4-dihydrocarbostyril monohydrochloride monohydrate
m.p. 273°–276° C. (decomp.), pale yellow powders 6-(3-Methylimidazo[1,2-a]pyridine-2-yl)-3,4-dihydrocarbostyril monohydrobromide hemihydrate
m.p. above 300° C., pale yellow needles
NMR (DMSO-d₆-D₂O)

| δ (ppm) = 8.65 (d, J = 7 Hz, 1H) |
|---|
| 8.06–7.73 (m, 2H) |
| 7.67–7.40 (m, 3H) |
| 7.23–7.03 (m, 1H) |
| 3.20–2.50 (m, 4H) |
| 2.72 (s, 3H) |

8-Methyl-6-(imidazo[1,2-a]pyridine-2-yl)-3,4-dihydrocarbostyril monohydrochloride 3/2 hydrate
m.p. above 300° C., pale brown powders
NMR (DMSO-d₆)

| δ (ppm) = 9.64 (s, 1H) |
|---|
| 8.86 (d, J = 7 Hz, 1H) |
| 8.70 (s, 1H) |
| 8.03–7.30 (m, 5H) |
| 3.10–2.83 (m, 2H) |
| 2.67–2.40 (m, 2H) |
| 2.32 (s, 3H) |

8-Chloro-6-(imidazo[1,2-a]pyridine-2-yl)-3,4-dihydrocarbostyril monohydrochloride hemihydrate
m.p. above 300° C., pale brown cottony crystals
NMR (DMSO-d₆)

| δ (ppm) = 9.70 (s, 1H) |
|---|
| 8.82 (d, J = 7 Hz, 1H) |
| 8.75 (s, 1H) |
| 8.05–7.23 (m, 5H) |
| 3.20–2.90 (m, 2H) |
| 2.73–2.40 (m, 2H) |

8-Methoxy-6-(imidazo[1,2-a]pyridine-2-yl)-3,4-dihydrocarbostyril monohydrobromide
m.p. 294.5°–296.0° C. (decomp.), pale yellow cottony crystals 6-(imidazo[1,2-a]pyridine-2-yl)carbostyril monohydrochloride
m.p. above 300° C., pale yellow cottony crystals
NMR (DMSO-d₆)

| δ (ppm) = 8.74 (d, J = 7 Hz, 1H) |
|---|
| 8.61 (s, 1H) |
| 8.31 (d, J = 2.5 Hz) |
| 8.17–7.10 (m, 6H) |
| 6.58 (d, J = 9 Hz, 1H) |

6-(3-Ethylimidazo[1,2-a]pyridine-2-yl)carbostyril monohydrobromide monohydrate
m.p. above 300° C., colorless cottony crystals NMR (DMSO-d₆-D₂O)

| δ (ppm) = 8.81 (d, J = 7 Hz, 1H) |
|---|
| 8.14 (d, J = 10 Hz, 1H) |
| 8.05–7.45 (m, 6H) |
| 6.69 (d, J = 10 Hz, 1H) |
| 3.45–3.00 (m, 2H) |
| 1.38 (t, J = 7.5 Hz, 3H) |

6-(Imidazo[1,2-a]pyridine-2-yl)-3,4-dihydrocarbostyril
m.p. 230°–232° C. (decomp.), colorless powders

EXAMPLE 4

To a suspension of 6-(imidazo[1,2-a]pyridine-2-yl)-3,4-dihydrocarbostyril (5 g) in dioxane (50 ml) was added DDQ (6.47 g) with stirring at 70° C. The reaction mixture was heated for 5 hours with stirring. After completion of reaction, the solvent was evaporated. The residue was extracted by the addition of chloroform and 0.5 N sodium hydroxide. The chloroform layer was washed with 0.5 N sodium hydroxide, washed with water and dried. After evaporating chloroform, the residue obtained was isolated and purified using silica gel column chromatography. Oily product obtained was dissolved in acetone and the solution was adjusted to pH of about 1 with concentrated hydrochloric acid. Crystals which formed were collected by filtration. The crude crystals thus obtained were recrystallized from water to give 2.4 g of 6-(imidazo[1,2-a]pyridine-2-yl)carbostyril monohydrochloride.
m.p. above 300° C., pale yellow cottony crystals
NMR (DMSO-d$_6$)

| |
|---|
| δ (ppm) = 8.74 (d, J = 7 Hz, 1H) |
| 8.61 (s, 1H) |
| 8.31 (d, J = 2.5 Hz) |
| 8.17–7.10 (m, 6H) |
| 6.58 (d, J = 9 Hz, 1H) |

EXAMPLE 5

In an analogous manner as in Example 4, 6-(3-ethylimidazo[1,2-a]pyridine-2-yl)carbostyril monohydrobromide monohydrate was prepared using appropriate starting materials.
m.p. above 300° C., colorless cottony crystals NMR (DMSO-d$_6$-D$_2$O)

| |
|---|
| δ (ppm) = 8.81 (d, J = 7 Hz, 1H) |
| 8.14 (d, J = 10 Hz, 1H) |
| 8.05–7.45 (m, 6H) |
| 6.69 (d, J = 10 Hz, 1H) |
| 3.45–3.00 (m, 2H) |
| 1.38 (t, J = 7.5 Hz, 3H) |

EXAMPLE 6

To a solution of 8-methyl-6-(3-methylimidazo[1,2-a]pyridine-2-yl)carbostyril (2 g) in 40 ml of methanol was added 10% palladium-carbon (0.2 g), and the mixture was subjected to catalytic reduction of 60° C. for 8 hours at a hydrogen gas pressure of 2 to 3 kg/cm$^2$. After completion of the reaction, the catalyst was removed by filtration and the filtrate was concentrated to dryness. The residue was dissolved in acetone and the solution was adjusted to pH of about 1 with concentrated hydrochloric acid. Crystals which precipitated were collected by filtration. The crude crystals thus formed were recrystallized from ethanol to give 1.2 g of 8-methyl-6-(3-methylimidazo[1,2-a]pyridine-2-yl)-3,4-dihydrocarbostyril monohydrochloride monohydrate.
m.p. 273°–276° C. (decomp.), pale yellow needles

EXAMPLE 7

In an analogous manner as in Example 6, the following compounds were prepared using appropriate starting materials.
6-(3-Methylimidazo[1,2-a]pyridine-2-yl)-3,4-dihydrocarbostyril monohydrobromide hemihydrate
m.p. above 300° C., pale yellow needles NMR (DMSO-d$_6$-D$_2$O)

| |
|---|
| δ (ppm) = 8.65 (d, J = 7Hz, 1H) |
| 8.06–7.73 (m, 2H) |
| 7.67–7.40 (m, 3H) |
| 7.23–7.03 (m, 1H) |
| 3.20–2.50 (m, 4H) |
| 2.72 (s, 3H) |

8-Methyl-6-(imidazo[1,2-a]pyridine-2-yl)-3,4-dihydrocarbostyril monohydrochloride 3/2 hydrate
m.p. above 300° C., pale brown powders
NMR (DMSO-d$_6$)

| |
|---|
| δ (ppm) = 9.64 (s, 1H) |
| 8.86 (d, J = 7Hz, 1H) |
| 8.70 (s, 1H) |
| 8.03–7.30 (m, 5H) |
| 3.10–2.83 (m, 2H) |
| 2.67–2.40 (m, 2H) |
| 2.32 (s, 3H) |

8-Chloro-6-(imidazo[1,2-a]pyridine-2-yl)-3,4-dihydrocarbostyril monohydrochloride hemihydrate
m.p. above 300° C., pale brown cottony crystals
NMR (DMSO-d$_6$)

| |
|---|
| δ (ppm) = 9.70 (s, 1H) |
| 8.82 (d, J = 7Hz, 1H) |
| 8.75 (s, 1H) |
| 8.05–7.23 (m, 5H) |
| 3.20–2.90 (m, 2H) |
| 2.73–2.40 (m, 2H) |

6-(3-Methylimidazo[1,2-a]pyridine-2-yl)-1-methyl-3,4-dihydrocarbostyril monohydrobromide
m.p. above 300° C., colorless powders
NMR (DMSO-d$_6$)

| |
|---|
| δ (ppm) = 8.85 (d, J = 7Hz, 1H) |
| 8.13–7.20 (m, 6H) |
| 3.33 (s, 3H) |
| 3.15–2.87 (m, 2H) |
| 2.73 (s, 3H) |
| 2.68–2.37 (m, 2H) |

8-Methoxy-6-(imidazo[1,2-a]pyridine-2-yl)-3,4-dihydrocarbostyril monohydrobromide
m.p. 294.5°–296.0° C. (decomp.), pale yellow cottony crystals

EXAMPLE 8

To a solution of 6-(3-methylimidazo[1,2-a]-pyridine-2-yl)-3,4-dihydrocarbostyril (3 g) in dimethylformamide (50 ml) was added 50% oily sodium hydride (590 mg) and the mixture was reacted for 2 hours at room temperature. Then, after adding methyl iodide (1.85 g), the mixture was further reacted for 3 hours at room temperature. After completion of reaction, dimethylformamide was evaporated. Chloroform and 0.5 N sodium hydroxide were added to the residue for extraction. The chloroform layer was washed with water thoroughly and dried followed by evaporation of chloroform. The residue was purified using silica gel column chromatography and the oily product thus obtained was dissolved in acetone. The solution was adjusted to pH of about 1 by the addition of 48% hydrobromic acid and crystals which formed were collected by filtration. The crude crystals thus obtained were recrystallized from water to give 2.9 g of 6-(3-methylimidazo[1,2-a]pyridine-2-yl)-1-methyl-3,4-dihydrocarbostyril monohydrobromide.
m.p. above 300° C., colorless powders
NMR (DMSO-d$_6$)

| |
|---|
| δ (ppm) = 8.85 (d, J = 7Hz, 1H), 8.13–7.20 (m, 6H), |
| 3.33 (s, 3H), 3.15–2.87 (m, 2H) |
| 2.73 (s, 3H), 2.68–2.37 (m, 2H) |

EXAMPLE 9

5-(α-bromobutyryl)-8-methoxy-3,4-dihydrocarbostyril (5 g), 2-aminopyridine (4.33 g) and acetonitrile (20 ml) were reacted by refluxing for 6 hours. The reaction mixture was concentrated to dryness and the residue was crystallized by the addition of water. The crystals were collected by filtration and washed with water. The crystals were dissolved in acetone and the solution was adjusted to pH of about 1 to 2 by the addition of 48% hydrobromic acid. Crystals which formed were collected by filtration. The crude crystals thus obtained were recrystallized from methanol-ether to give 3.73 g of 5-(3-ethylimidazo[1,2-a]pyridine-2-yl)-8-methoxy-3,4-dihydrocarbostyril monohydrobromide.

m.p. 254°–256.5° C., colorless powders

EXAMPLE 10

5-Chloroacetyl-8-methoxycarbostyril (5 g), 2-amino-4-picoline (6.45 g) and acetonitrile (40 ml) were reacted with refluxing for 3 hours, and the reaction mixture was cooled with ice water. Crystals which formed were collected by filtration. The crystals were suspended in acetone-methanol and the suspension was adjusted to pH of about 1 by the addition of concentrated hydrochloric acid. Crystals which formed were collected by filtration and recrystallized from methanol to give 4.0 g of 5-(7-methylimidazo[1,2-a]pyridine-2-yl)-8-methoxycarbostyril monohydrochloride 3/2 hydrate.

m.p. 269.5°–271.5° C. (decomp.), colorless powders

EXAMPLE 11

In an analogous manner as in Example 2, compounds shown below were prepared using appropriate starting materials.

5-(Imidazo[1,2-a]pyridine-2-yl)-8-methoxycarbostyril monohydrochloride monohydrate m.p. 256°–257.5° C. (decomp.), colorless cottony crystals (water)

5-(Imidazo[1,2-a]pyridine-2-yl)-8-methoxy-3,4-dihydrocarbostyril monohydrochloride hemihydrate m.p. 260°–261° C. (decomp.), colorless needles (methanol)

5-(3-Methylimidazo[1,2-a]pyridine-2-yl)-8-methoxycarbostyril monohydrobromide 3/2 hydrate m.p. 207.5°–210.0° C., pale yellow scales (methanol-ether)

5-(3-Methylimidazo[1,2-a]pyridine-2-yl)-8-methoxy-3,4-dihydrocarbostyril monohydrobromide m.p. 263°–264.5° C., pale yellow needles (methanol-ether)

5-(3-Ethylimidazo[1,2-a]pyridine-2-yl)-8-methoxycarbostyril monohydrobromide ¼ hydrate m.p. 229°–231.5° C., colorless powders (methanol-ether)

1-Methyl-5-(imidazo[1,2-a]pyridine-2-yl)-8-methoxy-3,4-dihydrocarbostyril monohydrochloride monohydrate m.p. 259°–260.5° C. (decomp.), colorless needles (methanol-ether)

5-(6-Chloroimidazo[1,2-a]pyridine-2-yl)-8-methoxycarbostyril monohydrochloride dihydrate m.p. 270°–272.5° C. (decomp.), colorless powders (methanol-ether)

5-(8-Methylimidazo[1,2-a]pyridine-2-yl)-8-methoxycarbostyril monohydrochloride monohydrate m.p. 255°–258.0° C. (decomp.), pale yellow cottony crystals (water)

5-(3,7-Dimethylimidazo[1,2-a]pyridine-2-yl)-8-methoxycarbostyril monohydrobromide monohydrate m.p. 249°–251° C., colorless prisms (methanol-ether)

5-(3-Methylimidazo[1,2-a]pyridine-2-yl)-8-hydroxycarbostyril monohydrochloride ¼ hydrate m.p. above 300° C., pale yellow cottony crystals (water)

| Elemental Analysis for $C_{16}H_{11}O_2N_3 \cdot HCl \cdot \frac{1}{4}H_2O$ | | | |
|---|---|---|---|
| | C | H | N |
| Calc'd (%): | 60.38 | 3.96 | 13.21 |
| Found (%): | 60.55 | 3.80 | 13.23 |

NMR(DMSO—$D_2O$)

$\delta$ (ppm) = 8.82 (d, J = 7.0, 1H)
8.43 (s, 1H)
8.18 (d, J = 10.0, 1H)
8.06–7.90 (m, 2H)
7.63–7.43 (m, 1H)
7.44 (d, J = 8.0, 1H)
7.23 (d, J = 8.0, 1H)
6.73 (d, J = 10.0, 1H)

5-(Imidazo[1,2-a]pyridine-2-yl)-8-hydroxy-3,4-dihydrocarbostyril monohydrochloride 3/2 hydrate m.p. above 300° C., colorless cottony crystals (water)

| Elemental Analysis for $C_{16}H_{13}O_2N_3 \cdot HCl \cdot 3/2H_2O$ | | | |
|---|---|---|---|
| | C | H | N |
| Calc'd (%): | 56.06 | 5.00 | 12.26 |
| Found (%): | 55.82 | 4.91 | 12.34 |

NMR (DMSO)

$\delta$ (ppm) = 9.02 (s, 1H)
8.93 (d, J = 7.0, 1H)
8.47 (s, 1H)
8.10–7.80 (m, 2H)
7.60–7.40 (m, 1H)
7.23 (d, J = 8.0, 1H)
7.01 (d, J = 8.0, 1H)
3.26–2.97 (m, 2H)
2.63–2.36 (m, 2H)

5-(3-Methyl-6-nitroimidazo[1,2-a]pyridine-2-yl)-8-methoxycarbostyril monohydrobromide m.p. 247.5°–250° C. (decomp.), yellow needles (methanol-ether)

5-(3-Methyl-8-hydroxyimidazo[1,2-a]pyridine-2-yl)-8-methoxycarbostyril monohydrochloride m.p. 266°–268° C. (decomp.), colorless powders (methanol-ether)

5-(8-Methoxyimidazo[1,2-a]pyridine-2-yl)-8-methoxycarbostyril monohydrochloride 5/2 hydrate m.p. 215.0°–216.5° C. (decomp.), colorless cottony crystals (water)

5-(3-Methyl-6,8-dibromoimidazo[1,2-a]pyridine-2-yl)-8-methoxycarbostyril monohydrobromide m.p. 246°–247° C. (decomp.), pale yellow needles (methanol)

1-Allyl-5-(imidazo[1,2-a]pyridine-2-yl)-8-methoxy-3,4-dihydrocarbostyril monohydrochloride m.p. 250°–252° C. (decomp.), colorless needles (methanol-ether)

1-Benzyl-5-(imidazo[1,2-a]pyridine-2-yl)-8-methoxy-3,4-dihydrocarbostyril monohydrochloride monohydrate m.p. 243.5°–245.5° C. (decomp.), colorless needles (ethanol)

1-Propargyl-5-(imidazo[1,2-a]pyridine-2-yl)-8-methoxy-3,4-dihydrocarbostyril monohydrochloride hemihydrate m.p. 241.5°–242.5° C. (decomp.), colorless needles (ethanol)

EXAMPLE 12

To a solution of 5-(imidazo[1,2-a]pyridine-2-yl)-8-methoxycarbostyril (4 g) in acetic acid (80 ml) was added dropwise at room temperature a solution of bromine (2.22 g) in acetic acid (5 ml). After completion of addition, the mixture was stirred for 3 hours. Crystals which precipitated were collected by filtration and washed with diethyl ether. The crystals thus obtained were dissolved in acetone and the solution was adjusted to pH of about 1 by the addition of 48% hydrobromic acid. Crystals which precipitated were collected by filtration and recrystallized from methanol-water to give 5 g of 5-(3-bromoimidazo[1,2-a]pyridine-2-yl)-8-methoxycarbostyril monohydrobromide monohydrate.

m.p. 245°–247.5° C. (decomp.), pale yellow needles

EXAMPLE 13

To a suspension of 5-(imidazo[1,2-a]pyridine-2-yl)-8-methoxy-3,4-dihydrocarbostyril (2.5 g) in 300 ml of water was added 1.71 ml of concentrated hydrochloric acid. The mixture was heated and the solution was cooled to 50° C. and 10 ml of aqueous solution having dissolved therein 0.65 g of sodium nitrite was added dropwise to the solution at 50° C. with stirring. After completion of addition, the reaction was continued for 2 hours and the reaction mixture was allowed to stand overnight at room temperature. Crystals which precipitated were collected by filtration, and recrystallized from methanol to give 1.9 g of 5-(3-nitrosoimidazo[1,2-a]pyridine-2-yl)-8-methoxy-3,4-dihydrocarbostyril.

m.p. 236.5°–238° C. (decomp.), green cottony crystals

EXAMPLE 14

To a suspension of 5-(3-nitrosoimidazo[1,2-a]-pyridine-2-yl)-8-methoxy-3,4-dihydrocarbostyril (20.85 g) in methanol (500 ml) was added 12 ml of concentrated hydrochloric acid to render the suspension acidic. 10% Palladium-carbon (2 g), was added to the suspension, and catalytic reduction was carried out at room temperature under atmospheric pressure. After completion of reaction, water was added to the reaction mixture to dissolve and the resulting mixture was heated. After removing the catalyst by filtration, the filtrate was concentrated to dryness. Acetone was added to the residue, and crystals which precipitated were collected by filtration and recrystallized from water to give 21.20 g of 5-(3-aminoimidazo[1,2-a]pyridine-2-yl)-8-methoxy-3,4-dihydrocarbostyril monohydrochloride hemihydrate.

m.p. 254.5°–257.0° C. (decomp.), pale yellow needles

EXAMPLE 15

A solution of 5-(3-aminoimidazo[1,2-a]pyridine-2-yl)-8-methoxy-3,4-dihydrocarbostyril (5 g) in 90% formic acid (10 ml) was heated at 100° C. for 2 hours. After completion of reaction, water was added to the reaction mixture followed by neutralizing with 1 N sodium hydroxide. Crystals which precipitated were collected by filtration, washed with methanol and recrystallized from chloroform-methanol to give 3.05 g of 5-(3-formylaminoimidazo[1,2-a]pyridine-2-yl)-8-methoxy-3,4-dihydrocarbostyril.

m.p. 303.5°–305° C. (decomp.), yellow prisms

EXAMPLE 16

A mixture of 5-{3-aminoimidazo[1,2-a]pyridine-2-yl}-8-methoxy-3,4-dihydrocarbostyril (5 g), 90% formic acid (15 ml) and 35% formalin (5 ml) was refluxed for 26 hours and the reaction mixture was concentrated to dryness. The residue was extracted by the addition of 1 N sodium hydroxide and chloroform. The chloroform layer was washed with water and dried followed by evaporating the solvent. The residue was passed through a silica gel column for isolation and crystals obtained were converted into hydrochloric acid salt in methanol. Recrystallization from methanol-ether gave 580 mg of 5-{3-dimethylaminoimidazo[1,2-a]pyridine-2-yl}-8-methoxy-3,4-dihydrocarbostyril monohydrochloride.

m.p. 242°–244.5° C. (decomp.), colorless prisms

EXAMPLE 17

To a solution of 5-(imidazo[1,2-a]pyridine-2-yl)-8-methoxycarbostyril (5 g) in acetic acid (50 ml) were added 50% aqueous solution of dimethylamine (1.7 g) and 35% aqueous solution of formalin (1.62 g). The mixture was stirred at 60° C. for 6 hours. After evaporating the solvent, the residue was extracted by the addition of chloroform and 0.5 N sodium hydroxide. The chloroform layer was washed with water and dried followed by evaporating the solvent. The residue was dissolved in methanol and the solution was adjusted to pH of about 1 by the addition of concentrated hydrochloric acid and concentrated to dryness. Acetone was added to the residue to precipitate crystals, which were collected by filtration. The crude crystals thus obtained were recrystallized from methanol-acetone to give 5-(3-dimethylaminomethylimidazo[1,2-a]pyridine-2-yl)-8-methoxycarbostyril dihydrochloride trihydrate.

m.p. 213.5°–216° C. (decomp.), colorless cottony crystals

EXAMPLE 18

To a suspension of 5-(3-dimethylaminomethylimidazo[1,2-a]pyridine-2-yl)-8-methoxycarbostyril (1.5 g) in acetonitrile (20 ml) was added methyl iodide (1.5 ml) and the mixture was stirred at 40° C. for 1 hour. Crystals thus formed were collected by filtration and recrystallized from water to give 1.7 g of 5-(3-trimethylammoniomethylimidazo[1,2-a]pyridine-2-yl)-8-methoxycarbostyril iodide trihydrate.

m.p. 136°–138° C. (decomp.), pale yellow granules

EXAMPLE 19

5-{3-Trimethylammoniomethylimidazo[1,2-a]-pyridine-2-yl}-8-methoxycarbostyril iodide (8 g) and sodium cyanide (3.2 g) were added to water (100 ml) and the mixture was refluxed for 5 hours. Crystals which precipitated were collected by filtration. After washing with methanol, the compound was converted into hydrochloric acid salt in methanol with concentrated hydrochloric acid and recrystallized from methanol-ether to give 3.6 g of 5-{3-carbamoylmethylimidazo[1,2-a]pyridine-2-yl}-8-methoxycarbostyril monohydrochloride 5/4 hydrate.

m.p. 250.5–251.5 (decomp.), colorless needles

EXAMPLE 20

A solution of 5-{3-trimethylammoniomethylimidazo[1,2-a]pyridine-2-yl}-8-methoxycarbostyril iodide (4.39 g) in water (40 ml) was refluxed while adding dropwise 10 ml of an aqueous solution having dissolved therein 440 mg of sodium cyanide. After completion of addition, the mixture was reacted for 30 minutes and then allowed to cool. Crystals which precipitated were collected by filtration and isolated by passing through a silica gel column. The crude crystals thus formed were recrystallized from methanol to give 0.85 g of 5-{3-cyanomethylimidazo[1,2-a]pyridine-2-yl}-8-methoxycarbostyril.

m.p. 261°–263° C. (decomp.), colorless prisms

EXAMPLE 21

A mixture of 5-{3-carbamoylmethylimidazo-[1,2-a]pyridine-2-yl}-8-methoxycarbostyril (1.6 g), potassium hydroxide (2.6 g), water (3 ml) and ethanol (9 ml) was refluxed for 1 hour. After completion of reaction, water was added to the reaction mixture, which was then treated with activated carbon and adjusted to pH of about 1 by the addition of concentrated hydrochloric acid followed by allowing to stand overnight. Crystals which precipitated were collected by filtration and recrystallized from dilute hydrochloric acid to give 0.9 g of 5-{3-carboxymethylimidazo[1,2-a]pyridine-2-yl}-8-methoxycarbostyril hemihydrate.

m.p. 259°–260.5° C. (decomp.), colorless needles

EXAMPLE 22

5-(Imidazo[1,2-a]pyridine-2-yl)-8-methoxy-3,4-dihydrocarbostyril (1.4 g) and DDQ (3.5 g) were added to dioxane (30 ml) and the mixture was refluxed for 5 hours. The reaction mixture was concentrated under reduced pressure and the residue was extracted by the addition of chloroform and 0.5 N sodium hydroxide. The chloroform layer was washed with 0.5 N sodium hydroxide and then with water twice. After drying, chloroform was evaporated. The residue was isolated and purified through a silica gel column. The crude crystals thus obtained were dissolved in acetone and hydrochloric acid was added to the resulting solution. Crystals which precipitated were collected by filtration and recrystallized from water to give 410 mg of 5-(imidazo[1,2-a]-pyridine-2-yl)-8-methoxycarbostyril monohydrochloride monohydrate.

m.p. 256°–257.5° C. (decomp.), colorless cottony crystals

EXAMPLE 23

To a solution of 5-(3-ethylimidazo[1,2-a]-pyridine-2-yl)-8-methoxycarbostyril (2 g) in methanol (50 ml) was added 10% palladium-carbon (0.2 g) and catalytic reduction was carried out for 6 hours at 50°–60° C. under a hydrogen gas pressure of 2 to 3 kg/cm². The catalyst was removed by filtration and the filtrate was concentrated to dryness. The residue was dissolved in acetone and hydrobromic acid was added to the solution. Crystals which precipitated were collected by filtration and the crude crystals thus obtained were recrystallized from methanol-ether to give 1.5 g of 5-(3-ethylimidazo-[1,2-a]pyridine-2-yl)-8-methoxy-3,4-dihydrocarbostyril monohydrobromide.

m.p. 254°–256.5° C., colorless powders

EXAMPLE 24

To a solution of 5-(imidazo[1,2-a]pyridine-2-yl)-8-methoxy-3,4-dihydrocarbostyril (3 g) in dimethylformamide (100 ml) was added 50% oily sodium hydride (600 mg) and the mixture was stirred for 2 hours at room temperature. After adding allyl bromide (1.48 g), the mixture was reacted for 3 hours at room temperature. The reaction mixture was concentrated to dryness and the residue was extracted by the addition of chloroform and 0.5 N sodium hydroxide. The chloroform layer was washed with water and dried followed by evaporation. The residue was purified using silica gel column chromatography and the oily product was dissolved in acetone and converted into hydrochloric acid salt by the addition of hydrochloric acid. Crystals which precipitated were collected by filtration and recrystallized from methanol-ether to give 1.76 g of 1-allyl-5-(imidazo-[1,2-a]pyridine-2-yl)-8-methoxy-3,4-dihydrocarbostyril monohydrochloride.

m.p. 250°–252° C. (decomp.), colorless needles

EXAMPLE 25

In an analogous manner as in Example 24, the following compounds were prepared using appropriate starting materials.

1-Benzyl-5-(imidazo[1,2-a]pyridine-2-yl)-8-methoxy-3,4-dihydrocarbostyril monohydrochloride monohydrate m.p. 243.5°–245.5° C. (decomp.), colorless needles (ethanol)

1-Propargyl-5-(imidazo[1,2-a]pyridine-2-yl)-8-methoxy-3,4-dihydrocarbostyril monohydrochloride hemihydrate m.p. 241.5°–242.5° C. (decomp.), colorless needles (ethanol)

1-Methyl-5-(imidazo[1,2-a]pyridine-2-yl)-8-methoxy-3,4-dihydrocarbostyril monohydrochloride monohydrate m.p. 259°–260.5° C. (decomp.), colorless needles (methanol-ether)

EXAMPLE 26

In an analogous manner as in Examples 2 and 6, the following compounds were prepared using appropriate starting materials.

6-(3,7-Dimethylimidazo[i,2-a]pyridine-2-yl)-carbostyril monohydrochloride hemihydrate m.p. above 300° C., colorless needles (methanol)
NMR (DMSO-$d_6$)

| | |
|---|---|
| $\delta$ (ppm): | 2.56 (s, 3H), 2.67 (s, 3H), |
| | 6.58 (d, J = 9Hz, 1H), |
| | 7.34 (bd, J = 7Hz, 1H), |
| | 7.49 (d, J = 8Hz, 1H), |
| | 7.64–8.11 (m, 4H), |
| | 8.59 (d, J = 7Hz, 1H) |

6-(5-Methylimidazo[1,2-a]pyridine-2-yl)carbostyril monohydrochloride m.p. above 300° C., pale yellow powder (methanol)
NMR (CF$_3$COOH)

| | |
|---|---|
| $\delta$ (ppm): | 2.94 (s, 3H), 7.30–7.55 (m, 2H), |
| | 7.83–8.17 (m, 3H), |
| | 8.23–8.47 (m, 2H), 8.53 (bs, 1H), |
| | 8.70 (d, J = 9Hz, 1H) |

6-(3-Dimethylaminomethylimidazo[1,2-a]pyridine-2-yl)carbostyril dihydrochloride trihydrate m.p. 204.5°–207° C. (decomp.), colorless needles (water)

6-(3-Trimethylammoniomethylimidazo[1,2-a]pyridine-2-yl)carbostyril iodide ¾ hydrate m.p. 185°–188.5° C. (decomp.) colorless powder (methanol-acetone)

6-(3-Nitrosoimidazo[1,2-a]pyridine-2-yl)carbostyril hemihydrate m.p. above 300° C., yellowish brown powder
NMR (CF₃COOH)-d₁)

| δ (ppm): | 7.24 (d, J = 9Hz, 1H), |
| --- | --- |
| | 7.83–8.07 (m, 2H), 8.25(d, J = 9H, 1H), |
| | 8.43–8.77 (m, 2H), |
| | 8.87 (dd, J = 9Hz, 2Hz, 1H), |
| | 9.12 (d, J = 2Hz, 1H), |
| | 9.88 (bd, J = 7Hz, 1H) |

6-(3-Aminoimidazo[1,2-a]pyridine-2-yl)carbostyril 6-(Imidazo[1,2-a]pyridine-2-yl)-1-propargylcarbostyril monohydrochloride ¾ hydrate m.p. 252°–253° C. (decomp.), colorless needles (water)

6-(3-Ethylimidazo[1,2-a]pyridine-2-yl)-3,4-dihydrocarbostyril monohydrobromide hemihydrate m.p. 314.5°–318° C. (decomp.), colorless cottony crystals (water)

6-(3-Ethylimidazo[1,2-a]pyridine-2-yl)-1-allyl-3,4-dihydrocarbostyril monohydrochloride m.p. 279°–282.5° C. (decomp.), colorless needles (ethanol)

6-(3-Ethylimidazo[1,2-a]pyridine-2-yl)-1-propargyl-3,4-dihydrocarbostyril monohydrochloride monohydrate m.p. 264°–265° C. (decomp.), colorless cottony crystals (water)

6-(3-Ethylimidazo[1,2-a]pyridine-2-yl)-1-propargylcarbostyril monochloride ¼ hydrate m.p. 265°–266° C. (decomp.), colorless needles (water)

5-(8-hydroxyimidazo[1,2-a]pyridine-2-yl)-8-methoxycarbostyril monohydrochloride m.p. 266.5°–268.5° C. (decomp.), colorless powders (methanol-ether)

EXAMPLE 27

In an analogous manner as in Example 4, the following compounds were prepared using appropriate starting materials.

6-(3,7-Dimethylimidazo[1,2-a]pyridine-2-yl)-carbostyril monohydrochloride hemihydrate m.p. above 300° C., colorless needles (methanol)
NMR (DMSO-d₆)

| (ppm): | 2.56 (s, 3H), 2.67 (s, 3H), |
| --- | --- |
| | 6.58 (d, J = 9Hz, 1H), |
| | 7.34 (bd, J = 7Hz, 1H), |
| | 7.49 (d, J = 8Hz, 1H), |
| | 7.64–8.11 (m, 4H), |
| | 8.59 (d, J = 7Hz, 1H) |

6-(5-Methylimidazo[1,2-a]pyridine-2-yl)carbostyril monohydrochloride m.p. above 300° C., pale yellow powder (methanol)
NMR (CF₃COOH-d₁)

| δ(ppm): | 2.94 (s, 3H), 7.30–7.55 (m, 2H), |
| --- | --- |
| | 7.83–8.17 (m, 3H), |
| | 8.23–8.47 (m, 2H), 8.53 (bs, 1H), |
| | 8.70 (d, J = 9Hz, 1H) |

6-(3-Dimethylaminomethylimidazo[1,2-a]pyridine-2-yl)carbostyril dihydrochloride trihydrate m.p. 204.5°–207° C. (decomp.), colorless needles (water)

6-(3-Trimethylammoniomethylimidazo[1,2-a]pyridine-2-yl)carbostyril iodide ¾ hydrate m.p. 185°–188.5° C. (decomp.), colorless powder (methanol-acetone)

6-(3-Nitrosoimidazo[1,2-a]pyridine-2-yl)carbostyril hemihydrate m.p. above 300° C., yellowish brown powder
NMR (CF₃COOH-d₁)

| δ(ppm): | 7.24 (d, J = 9Hz, 1H), |
| --- | --- |
| | 7.83–8.07 (m, 2H), |
| | 8.25 (d, J = 9Hz, 1H), |
| | 8.43–8.77 (m, 2H), |
| | 8.77 (dd, J = 9Hz, 2Hz, 1H), |
| | 9.12 (d, J = 2Hz, 1H), |
| | 9.88 (bd, J = 7Hz, 1H) |

6-(3-Aminoimidazo[1,2-a]pyridine-2-yl)carbostyril 6-(Imidazo[1,2-a]pyridine-2-yl)-1-propargylcarbostyril monochloride ¾ hydrate m.p. 252°–253° C. (decomp.), colorless needles (water)

6-(3-Ethylimidazo[1,2-a]pyridine-2-yl)-3,4-dihydrocarbostyril monohydrobromide hemihydrate m.p. 314.5°–318° C. (decomp.), colorless cottony crystals (water)

6-(3-Ethylimidazo[1,2-a]pyridine-2-yl)-1-propargylcarbostyril monohydrochloride ¼ hydrate m.p. 265°–266° C. (decomp.), colorless needles (water)

5-(8-Hydroxyimidazo[1,2-a]pyridine-2-yl)-8-methoxycarbostyril monohydrochloride m.p. 266.5°–268.5° C. (decomp.), colorless powders (methanol-ether)

EXAMPLE 28

In an analogous manner as in Example 8, the following compounds were prepared using appropriate starting materials.

6-(3-Ethylimidazo[1,2-a]pyridine-2-yl)-1-allyl-3,4-dihydrocarbostyril monohydrochloride m.p. 279°–282.5° C. (decomp.), colorless needles (ethanol)

6-(3-Ethylimidazo[1,2-a]pyridine-2-yl)-1-propargyl-3,4-dihydrocarbostyril monohydrochloride monohydrate m.p. 264°–265° C. (decomp.), colorless cottony crystals (water)

6-(3-Ethylimidazo[1,2-a]pyridine-2-yl)-1-propargylcarbostyril monochloride ¼ hydrate m.p. 265°–266° C. (decomp.), colorless needles (water)

6-(Imidazo[1,2-a]pyridine-2-yl)-1-propargylcarbostyril monohydrochloride ¾ hydrate m.p. 252°–253° C. (decomp.), colorless needles (water)

EXAMPLE 29

Pharmacological activity of the compounds of this invention was determined as described below.

Isolated blood-perfused sinoatrial node preparations

Experiments were carried out on adult mongrel dogs of either sex. The sinoatrial node preparations were obtained from dogs weighing 8–13 kg, anesthetized with pentobarbital sodium (30 mg/kg i.v.), given heparin sodium (1,000 U/kg i.v.) and exsanquinated. The preparation consisted essentially of the right atrium and was set up on cold Tyrode's solution. The preparation was placed in a glass water jacket maintained at about 38° C. and corss-circulated through the cannulated right coronary artery with blood from a donor dog at a constant pressure of 100 mm Hg. Dogs used as donors were 18–27 kg in body weight and were anesthetized with pentobarbital sodium (30 mg/kg i.v.). Heparin sodium was given at a dose of 1,000 U/kg i.v. Tension developed by the right atrium was measured with a strain-gauge transducer. The right atrium was loaded with a weight of about 1.5 g. Sinus rate was measured by a cardiotachometer triggered by developed tension of the right atrium. Blood flow through the right coronary artery was measured by an electromagnetic flow meter. Recording of developed tension, sinus rate and blood flow was made on charts with an ink-writing rectigraph. Details of the preparation have been described by Chib et al. (Japan. J. Pharmacol., 25, 433–439, 1975; Naunyn-Schmiedberg's Arch. Pharmacol., 289, 315–325, 1975). The compounds of 10–30 μl were injected intra-arterially in 4 sec. The inotropic effects of the compounds are expressed as a percentage of the developed tension before the injection of the compounds. The effects of the compounds on sinus rate (beats/min) or blood flow (ml/min) are expressed as a difference between the values before and after the injection of the compounds.

The results obtained are shown in Table 1 below.

Test Compounds 1. 6-(3-Methylimidazo[1,2-a]pyridine-2-yl)-1-methyl-3,4-dihydrocarbostyril monohydrobromide
2. 8-Methoxy-4-(3-methylimidazo[1,2-a]pyridine-2-yl)-3,4-dihydrocarbostyril monohydrobromide
3. 5-(3-Methyl-6,8-dibromoimidazo[1,2-a]pyridine-2-yl)-8-methoxycarbostyril monohydrobromide
4. 1-Propargyl-5-(imidazo[1,2-a]pyridine-2-yl)-8-methoxycarbostyril monohydrochloride hemihydrate
5. 5-(3,7-Dimethylimidazo[1,2-a]pyridine-2-yl)-8-methoxycarbostyril monohydrobromide monohydrate
6. 5-(3-Ethylimidazo[1,2-a]pyridine-2-yl)-8-methoxycarbostyril monohydrobromide ¼ hydrate
7. 1-Methyl-5-(imidazo[1,2-a]pyridine-2-yl)-8-methoxy-3,4-dihydrocarbostyril monohydrochloride
8. 5-(6-Chloroimidazo[1,2-a]pyridine-2-yl)-8-methoxycarbostyril monohydrochloride dihydrate
9. 5-(7-Methylimidazo[1,2-a]pyridine-2-yl)-8-methoxycarbostyril monohydrochloride 3/2 hydrate
10. 5-(3-Dimethylaminoimidazo[1,2-a]pyridine-2-yl)-8-methoxycarbostyril dihydrochloride trihydrate
11. 1-Allyl-5-(Imidazo[1,2-a]pyridine-2-yl)-8-methoxy-3,4-dihydrocarbostyril monohydrochloride
12. 5-(Imidazo[1,2-a]pyridine-2-yl)-8-hydroxycarbostyril monohydrochloride
13. 6-(Imidazo[1,2-a]pyridine-2-yl)carbostyril monohydrochloride
14. 6-(3-Ethylimidazo[1,2-a]pyridine-2-yl)carbostyril monohydrobromide monohydrate
15. 5-(3-Methyl-6-nitroimidazo[1,2-a]pyridine-2-yl)-8-methoxycarbostyril
16. 5-(3-Bromoimidazo[1,2-a]pyridine-2-yl)-8-methoxycarbostyril monohydrobromide monohydrate
17. 5-(8-Hydroxyimidazo[1,2-a]pyridine-2-yl)-8-methoxycarbostyril
18. 5-(8-Methoxyimidazo[1,2-a]pyridine-2-yl)-8-methoxycarbostyril monohydrochloride 5/2 hydrate
19. 5-(Imidazo[1,2-a]pyridine-2-yl)-8-methoxycarbostyril monohydrochloride
20. 6-(Imidazo[1,2-a]pyridine-2-yl)-3,4-dihydrocarbostyril monohydrochloride
21. 6-(3-Methylimidazo[1,2-a]pyridine-2-yl)-8-methyl-3,4-dihydrocarbostyril monohydrochloride monohydrate
22. 5-(3-Ethylimidazo[1,2-a]pyridine-2-yl)-8-methoxy-3,4-dihydrocarbostyril monohydrobromide
23. 5-(3-Methylimidazo[1,2-a]pyridine-2-yl)-8-methoxy-3,4-dihydrocarbostyril monohydrobromide
24. 5-(3-Methylimidazo[1,2-a]pyridine-2-yl)-8-methoxycarbostyril monohydrobromide hemihydrate
25. 5-(Imidazo[1,2-a]pyridine-2-yl)-8-methoxy-3,4-dihydrocarbostyril monohydrochloride 3/2 hydrate
26. 6-(3-Methylimidazo[1,2-a]pyridine-2-yl)-3,4-dihydrocarbostyril monohydrobromide hemihydrate
27. 6-(3-Methylimidazo[1,2-a]pyridine-2-yl)-8-chloro-3,4-dihydrocarbostyril monohydrobromide hemihydrate
28. 5-(3-Nitrosoimidazo[1,2-a]pyridine-2-yl)-8-methoxy-3,4-dihydrocarbosytril
29. 5-(3-Aminoimidazo[1,2-a]pyridine-2-yl)-8-methoxy-3,4-dihydrocarbostyril monohydrochloride hemihydrate
30. 5-(3-Trimethylammoniomethylimidazo[1,2-a]pyridine-2-yl)-8-methoxycarbostyril iodide trihydrate
31. 5-(3-Carbamoylmethylimidazo[1,2-a]pyridine-2-yl)-8-methoxycarbostyril monohydrochloride 5/4 hydrate
32. 5-(3-Cyanomethylimidazo[1,2-a]pyridine-2-yl)-8-methoxycarbostyril
33. 5-(3-Carboxymethylimidazo[1,2-a]pyridine-2-yl)-8-methoxycarbostyril hemihydrate a. Isoprenalin (Comparison)
b. Amrinone (Comparison)

TABLE 1

| Test Compound | Dose (μ mole/l) | % Change in Contraction of Atrial Muscle | Change in Rate of Coronary Blood Flow (ml/min) |
| --- | --- | --- | --- |
| 1 | 1 | 77.7 | 3.6 |
| 2 | 1 | 129.4 | 1.6 |
| 3 | 0.3 | 41.2 | 1.8 |
| 4 | 1 | 63.2 | 2.4 |
| 5 | 1 | 109.1 | 4.0 |
| 6 | 1 | 61.5 | 2 |
| 7 | 1 | 45.8 | 1.5 |
| 8 | 0.3 | 18.2 | 1.2 |
| 9 | 0.3 | 14.3 | — |
| 10 | 1 | 53.3 | 2.0 |
| 11 | 1 | 50.0 | 2.6 |
| 12 | 1 | 18.8 | 2.4 |
| 13 | 0.1 | 40.6 | 1.6 |
| 14 | 0.03 | 71.4 | 1.8 |
| 15 | 0.3 | 35.7 | 1.4 |
| 16 | 0.3 | 10.0 | — |
| 17 | 0.3 | 38.5 | 0.8 |
| 18 | 0.3 | 14.5 | — |
| 19 | 1 | 89.7 | 2.8 |
| 20 | 1 | 105 | 3.5 |
| 21 | 0.1 | 81.2 | 2.0 |
| 22 | 0.3 | 25 | 0.8 |
| 23 | 1 | 104.2 | 1.0 |
| 24 | 1 | 84.6 | 0.4 |
| 25 | 1 | 95 | 1.2 |
| 26 | 0.3 | 123.3 | 2.4 |
| 27 | 1 | 194.7 | 2.0 |
| 28 | 0.1 | 18.8 | — |
| 29 | 1 | 37 | 1.6 |
| 30 | 0.3 | 40 | 0.6 |
| 31 | 0.3 | 13 | 0.8 |
| 32 | 0.3 | 73 | 1.2 |
| 33 | 0.1 | 20 | — |

TABLE 1-continued

| Test Compound | Dose (μ mole/l) | % Change in Contraction of Atrial Muscle | Change in Rate of Coronary Blood Flow (ml/min) |
|---|---|---|---|
| a | $1 \times 10^{-5}$ | 84.8 | 3 |
| b | 1 | 86.4 | 4.8 |

PREPARATION EXAMPLE 1

| | |
|---|---|
| 8-Methoxy-(3-methylimidazo[1,2-a]-pyridine-2-yl)-3,4-dihydrocarbostyril monohydrobromide | 5 mg |
| Starch | 132 mg |
| Magnesium stearate | 18 mg |
| Lactose | 45 mg |
| Total | 200 mg |

In a conventional manner, tablets having the above composition were prepared.

PREPARATION EXAMPLE 2

| | |
|---|---|
| 6-(3-Methylimidazo[1,2-a]pyridine-2-yl)-1-methyl-3,4-dihydrocarbostyril monohydrobromide | 10 mg |
| Starch | 127 mg |
| Magnesium stearate | 18 mg |
| Lactose | 45 mg |
| Total | 200 mg |

In a conventional manner, tablets having the above composition were prepared.

PREPARATION EXAMPLE 3

| | |
|---|---|
| 8-Chloro-6-(3-methylimidazo[1,2-a]-pyridine-2-yl)-3,4-dihydrocarbo-styril monohydrobromide hemihydrate | 500 mg |
| Polyethylene glycol (molecular weight: 4,000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the distilled water at 80° C. while stirring. The resulting solution was cooled to 40° C. and polyethylene glycol and polyoxyethylene sorbitan monooleate were dissolved therein. Then, distilled water for injection was added to adjust the volume to final one. The mixture was filtered using a suitable filter paper to sterilize and then filled in an ampoule of 1 ml, thus forming preparation for injection.

PREPARATION EXAMPLE 4

| | |
|---|---|
| 1-Methyl-5-(imidazo[1,2-a]pyridine-2-yl)-8-methoxy-3,4-dihydrocarbostyril monohydrochloride monohydrate | 5 mg |
| Starch | 132 mg |
| Magnesium stearate | 18 mg |
| Lactose | 45 mg |
| Total | 200 mg |

Tablets each having the above composition were prepared in a conventional manner.

PREPARATION EXAMPLE 5

| | |
|---|---|
| 5-(6-Chloroimidazo[1,2-a]pyridine-2-yl)-8-methoxycarbostyril monohydrochloride dihydrate | 10 mg |
| Starch | 127 mg |
| Magnesium stearate | 18 mg |
| Lactose | 45 mg |
| Total | 200 mg |

Tablets each having the above composition were prepared in a conventional manner.

PREPARATION EXAMPLE 6

| | |
|---|---|
| 5-(3,7-Dimethylimidazo[1,2-a]pyridine-2-yl)-8-methoxycarbostyril monohydrobromide monohydrate | 500 mg |
| Polyethylene glycol (molecular weight: 4,000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the distilled water at 80° C. while stirring. The resulting solution was cooled to 46° C. and polyethylene glycol and polyoxyethylene sorbitan monooleate were dissolved therein. Then, distilled water for injection was added to adjust the volume to final one. The mixture was filtered using a suitable filter paper to sterilize and then filled in an ampoule of 1 ml, thus forming preparation for injection.

INDUSTRIAL APPLICABILITY

As described above, the carbostyril compounds and the pharmaceutically acceptable salts thereof are useful as a cardiotonic agent for treating heart diseases such as congestive heart failure and the like.

What is claimed is:

1. A carbostyril compound of the formula (I)

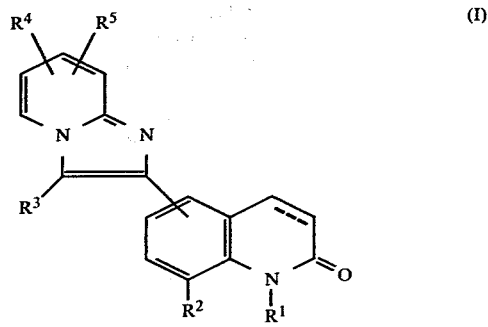

wherein $R^1$ represents a hydrogen atom, a lower alkyl group, a lower alkenyl group, a lower alkynyl group, or a phenyl-lower alkyl group;

$R^2$ represents a hydrogen atom, a lower alkyl group, a lower alkoxy group, a halogen atom, or a hydroxy group;

R³ represents a hydrogen atom, a lower alkyl group, a halogen atom, a nitroso group, an amino group which may be substituted with a lower alkyl group, a lower alkanoylamino group, an N,N-di-lower alkylaminomethyl group, a carbamoylmethyl group, a cyanomethyl group, or a carboxymethyl group;

R⁴ and R⁵, which may be the same or different, each represents a hydrogen atom, a halogen atom, a lower alkyl group, a hydroxy group, a lower alkoxy group, or a nitro group;

the bonding between the 3- and 4-positions of the carbostyril nucleus is a single bond or a double bond; and the position at which the imidazopyridyl group of the formula

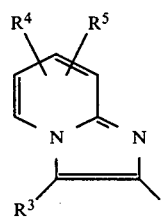

is attached to the carbostyril nucleus is the 5- or 6-position;

with the proviso that when the imidazopyridyl group is attached to the 5-position of the carbostyril nucleus, R² should not be a hydrogen atom, a lower alkyl group, or a halogen atom; or its pharmaceutically acceptable salt.

2. A compound or its pharmaceutically acceptable salt as claimed in claim 1, wherein the substituent of the formula

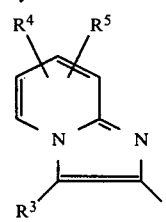

is attached to the 5-position of the carbostyril nucleus.

3. A compound or its pharmaceutically acceptable salt as claimed in claim 1, wherein the substituent of the formula

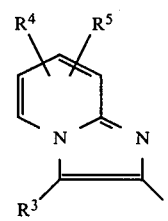

is attached to the 6-position of the carbostyril nucleus.

4. A compound or its pharmaceutically acceptable salt as claimed in claim 2 or 3, wherein R¹ represents a hydrogen atom.

5. A compound or its pharmaceutically acceptable salt as claimed in claim 2 or 3, wherein R¹ represents a lower alkyl group, a phenyl-lower alkenyl group, a lower alkylthio group, or a lower alkynyl group.

6. 5-(3,7-Dimethylimidazo[1,2-a]pyridine-2-yl)-8-methoxycarbostyril or its pharmaceutically acceptable salt according to claim 4.

7. 5-(3-Methyl-6-nitroimidazo[1,2-a]pyridine-2-yl)-8-methoxycarbostyril or its pharmaceutically acceptable salt according to claim 4.

8. 5-(3-Ethylimidazo[1,2-a]pyridine-2-yl)-8-methoxycarbostyril or its pharmaceutically acceptable salt according to claim 4.

9. 1-Allyl-5-(imidazo[1,2-a]pyridine-2-yl)-8-methoxy-3,4-dihydrocarbostyril or its pharmaceutically acceptable salt according to claim 5.

10. 1-Propargyl-5-(imidazo[1,2-a]pyridine-2-yl)-8-methoxy-3,4-dihydrocarbostyril or its pharmaceutically acceptable salt according to claim 5.

11. 6-(Imidazo[1,2-a]pyridine-2-yl)-3,4-dihydrocarbostyril or its pharmaceutically acceptable salt according to claim 4.

12. 8-Chloro-6-(3-methylimidazo[1,2-a]pyridine-2-yl)-3,4-dihydrocarbostyril or its pharmaceutically acceptable salt according to claim 4.

13. 8-Methoxy-6-(imidazo[1,2-a]pyridine-2-yl)-3,4-dihydrocarbostyril or its pharmaceutically acceptable salt according to claim 4.

14. 5-(3-Methylimidazo[1,2-a]pyridine-2-yl)-8-methoxycarbostyril or its pharmaceutically acceptable salt according to claim 4.

15. 8-Methyl-6-(3-methylimidazo[1,2-a]pyridine-2-yl)-3,4-dihydrocarbostyril or its pharmaceutically acceptable salt according to claim 4.

16. 8-Methoxy-5-(imidazo[1,2-a]pyridine-2-yl)-carbostyril or its pharmaceutically acceptable salt according to claim 4.

17. A cardiotonic composition comprising a cardiotonically effective amount of a compound of the formula (I)

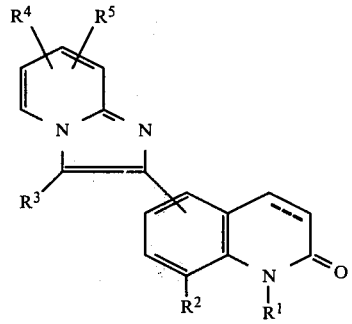

wherein R¹ represents a hydrogen atom, a lower alkyl group, a lower alkenyl group, a lower alkynyl group, or a phenyl-lower alkyl group;

R² represents a hydrogen atom, a lower alkyl group, a lower alkoxy group, a halogen atom, or a hydroxy group;

R³ represents a hydrogen atom, a lower alkyl group, a halogen atom, a nitroso group, an amino group which may be substituted with a lower alkyl group, a lower alkanoylamino group, an N,N-di-lower alkylaminomethyl group, a carbamoylmethyl group, a cyanomethyl group, or a carboxymethyl group;

R⁴ and R⁵, which may be the same or different, each represents a hydrogen atom, a halogen atom, a lower alkyl group, a hydroxy group, a lower alkoxy group, or a nitro group;

the bonding between the 3- and 4-positions of the carbostyril nucleus is a single bond or a double bond; and the position at which the imidazopyridyl group of the formula

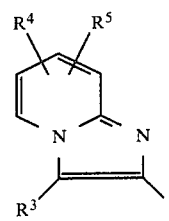

is attached to the carbostyril nucleus is the 5- or 6-position;

with the proviso that when the imidazopyridyl group is attached to the 5-position of the carbostyril nucleus, $R^2$ should not be a hydrogen atom, a lower alkyl group, or a halogen atom; or its pharmaceutically acceptable salt as active ingredient and a pharmaceutically acceptable carrier.

* * * * *